US007774072B2

(12) United States Patent
Gerber

(10) Patent No.: US 7,774,072 B2
(45) Date of Patent: Aug. 10, 2010

(54) ATTACHED IMPLANTABLE MEDICAL ELONGATED MEMBERS

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 580 days.

(21) Appl. No.: 11/606,625

(22) Filed: Nov. 30, 2006

(65) Prior Publication Data

US 2008/0132980 A1    Jun. 5, 2008

(51) Int. Cl.
   *A61N 1/00* (2006.01)
(52) U.S. Cl. ...................................................... 607/116
(58) Field of Classification Search ................ 607/117, 607/118, 116, 123, 126, 127, 133, 39, 46; 600/377; 606/129
   See application file for complete search history.

(56) References Cited

U.S. PATENT DOCUMENTS

| | | | |
|---|---|---|---|
| 4,332,259 A | | 6/1982 | McCorkle, Jr. |
| 4,643,201 A | * | 2/1987 | Stokes ......................... 607/122 |
| 5,282,845 A | | 2/1994 | Bush et al. |
| 5,458,631 A | * | 10/1995 | Xavier ......................... 607/117 |
| 5,769,881 A | | 6/1998 | Schroeppel et al. |
| 5,813,979 A | | 9/1998 | Wolfer |
| 5,938,596 A | * | 8/1999 | Woloszko et al. ............ 600/377 |
| 6,505,075 B1 | | 1/2003 | Weiner |
| 6,544,270 B1 | * | 4/2003 | Zhang ......................... 606/129 |
| 6,587,733 B1 | | 7/2003 | Cross, Jr. et al. |
| 6,597,953 B2 | | 7/2003 | Boling |
| 6,639,153 B2 | | 10/2003 | Hauge |
| 6,743,055 B1 | | 6/2004 | Flynn et al. |
| 6,772,015 B2 | | 8/2004 | Dahl et al. |
| 6,876,885 B2 | | 4/2005 | Swoyer et al. |

(Continued)

FOREIGN PATENT DOCUMENTS

EP            0 479 435 A2    4/1992

(Continued)

OTHER PUBLICATIONS

Notification of Transmittal of the International Preliminary Report on Patentability for corresponding patent application No. PCT/US2007/008588, mailed Oct. 28, 2008, 11 pages.
Notification of Transmittal of the International Search Report and the Written Opinion of the International Searching Authority for corresponding patent application No. PCT/US2007/008588, mailed Nov. 2, 2007, 11 pages.
Communication Pursuant to Article 94(3) EPC, dated Mar. 11, 2010, for European patent application No. 07 755 055.1-2305, 2 pages.

*Primary Examiner*—George Manuel
*Assistant Examiner*—Robert N Wieland
(74) *Attorney, Agent, or Firm*—Shumaker & Sieffert, P.A.

(57) ABSTRACT

An assembly comprises at least two elongated members that are attached together via one or more attachment elements such that the elongated members each define unattached distal branches. The elongated members are configured to deliver a therapy from a medical device to at least one target tissue site within a patient. Each elongated member may deliver the therapy to a different target tissue site.

36 Claims, 9 Drawing Sheets

U.S. PATENT DOCUMENTS

| | | |
|---|---|---|
| 6,909,918 B2 | 6/2005 | Stypulkowski |
| 7,072,719 B2 | 7/2006 | Vinup et al. |
| 2002/0198572 A1* | 12/2002 | Weiner .................. 607/46 |
| 2004/0093051 A1* | 5/2004 | Chinn et al. ............ 607/116 |
| 2004/0162544 A1 | 8/2004 | Raulerson et al. |
| 2005/0004639 A1* | 1/2005 | Erickson ................ 607/122 |
| 2005/0228249 A1 | 10/2005 | Boling |
| 2006/0161235 A1 | 7/2006 | King |
| 2006/0264777 A1 | 11/2006 | Drew |

FOREIGN PATENT DOCUMENTS

| | | |
|---|---|---|
| EP | 0 865 800 A2 | 9/1998 |
| EP | 1 048 319 A2 | 11/2000 |
| WO | WO98/52641 | 11/1998 |
| WO | WO2004/103462 A1 | 12/2004 |
| WO | WO2004/103468 A1 | 12/2004 |
| WO | WO2004/105640 A2 | 12/2004 |
| WO | WO2005/028025 A1 | 3/2005 |

* cited by examiner

ATTACHED IMPLANTABLE MEDICAL ELONGATED MEMBERS

TECHNICAL FIELD

The invention relates to medical device systems and, more particularly, to elongated members in medical device systems.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. An electrical stimulation system typically includes one or more implantable medical leads coupled to an external or implantable electrical stimulator.

The implantable medical lead may be percutaneously or surgically implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, stomach, bladder, or within a brain or other organ of a patient, or within a muscle or muscle group of a patient. The one or more electrodes located proximate to the target stimulation site may deliver electrical stimulation therapy to the target stimulation site in the form of electrical signals. Additionally or alternatively, one or more electrodes may sense one or more physiological signals and/or patient conditions.

Electrical stimulation of a sacral nerve may eliminate or reduce some pelvic floor disorders by influencing the behavior of the relevant structures, such as the bladder, sphincter and pelvic floor muscles. Pelvic floor disorders include urinary incontinence, urinary urge/frequency, urinary retention, pelvic pain, bowel dysfunction, and male and female sexual dysfunction. The organs involved in bladder, bowel, and sexual function receive much of their control via the second, third, and fourth sacral nerves, commonly referred to as S2, S3 and S4, respectively. Thus, in order to deliver electrical stimulation to at least one of the S2, S3, or S4 sacral nerves, an implantable medical lead is implanted proximate to the sacral nerve(s).

Electrical stimulation of a peripheral nerve, such as stimulation of an occipital nerve, may be used to mask a patient's feeling of pain with a tingling sensation, referred to as paresthesia. Occipital nerves, such as a lesser occipital nerve, greater occipital nerve or third occipital nerve, exit the spinal cord at the cervical region, extend upward and toward the sides of the head, and pass through muscle and fascia to the scalp. Pain caused by an occipital nerve, e.g. occipital neuralgia, may be treated by implanting a lead proximate to the occipital nerve to deliver stimulation therapy.

In many electrical stimulation applications, it is desirable to delivery therapy to two or more locations, such as similar locations on both the left and right sides of the body. Often two leads, each with a set of one or more electrodes, are implanted to deliver bilateral stimulation.

SUMMARY

In general, the invention relates to an assembly including at least two implantable medical elongated members that are attached together at one or more points to define at least two unattached distal branches of the elongated members. Each elongated member includes an elongated body extending between a proximal end that is configured to couple directly or indirectly (e.g., via an extension) to an external or implantable medical device and a distal end. The elongated members are configured to deliver a therapy, such as electrical stimulation, drug delivery, parameter sensing, or combinations thereof, from the medical device to at least two target tissue sites within a patient. Accordingly, the elongated members may take the form of electrical leads and/or fluid delivery conduits. The distal branches of the elongated members are configured to be implanted at separate tissue sites within a patient. However, in some embodiments, the distal branches may be implanted at the same or overlapping target tissue sites.

Attaching a first portion of a first elongated body to a second portion of a second elongated body may help fix a distance between the elongated bodies, may help simplify the implantation process, and may also help prevent the elongated bodies from unintentionally crossing over each other. In some cases, intentional cross-over between the elongated bodies may be desirable. However, unintentional crossover the elongated bodies may be undesirable and may have detrimental effects on the quality of therapy delivered to a patient and/or may cause patient discomfort. For example, the elongated members may experience increased contact (e.g., rubbing) in regions of cross-over, which may cause wear-through or damage to the elongated bodies of the elongated members. Contact between elongated members may also occur in regions other than regions of cross-over, such as regions in which the first and second elongated bodies are not in a fixed relationship with respect to each other.

In one embodiment, the invention is directed toward a medical device system comprising a first implantable medical elongated member configured to couple to a medical device and deliver a therapy from the medical device to a first target tissue site in a patient, the first elongated member comprising a first distal end, a second implantable medical elongated member configured to couple to the medical device and deliver the therapy from the medical device to a second target tissue site in the patient, the second elongated member comprising a second distal end, and an attachment element coupled to attach the first elongated member and the second elongated member at an attachment point. The first elongated member defines a first branch extending between the attachment element and the first distal end, and the second elongated member defines a second branch extending between the attachment element and the second distal end. The first branch and the second branch are unattached.

In one embodiment, the invention is directed toward a medical device system comprising a first implantable medical elongated member configured to couple to a first medical device and comprising a first distal end, a second implantable medical elongated member configured to couple to a second medical device and comprising a second distal end, and an attachment element coupled to attach the first elongated member and the second elongated member at an attachment point. The first elongated member defines a first branch extending between the attachment element and the first distal end, and the second elongated member defines a second branch extending between the attachment element and the second distal end. The first branch and the second branch are unattached.

In another embodiment, the invention is directed toward a method comprising inserting a first implantable medical elongated member within a patient such that a first distal end of the first elongated member resides at a first target tissue site within the patient, inserting a second implantable medical elongated member within a patient such that a second distal end of second elongated member resides at a second target tissue site within the patient, and coupling an attachment element to the first and second elongated members at an attachment point displaced from the first distal end of the first elongated member and the second distal end of the second elongated member such that the first and second elongated members define respective branches extending between the attachment point and the first and second target tissue sites.

In another embodiment, the invention is directed toward a method comprising inserting a first lead configured to deliver electrical stimulation from an electrical stimulator to a first target tissue site in an occipital region of a patient into a body of the patient. The first lead comprises a first lead body extending between a first proximal end configured to couple to the electrical stimulator and a first distal end, and a first electrode proximate to the first distal end. The method further comprises inserting a second lead configured to deliver electrical stimulation from the electrical stimulator to a second target tissue site in the occipital region of the patient into the body of the patient. The second lead comprises a second lead body extending between a second proximal end configured to couple to the medical device and a second distal end, and a second electrode proximate to the second distal end. The method further comprises coupling an attachment element to the first and second lead bodies an attachment point displaced from the first distal end of the first lead body and the second distal end of the second lead body such that the first and second lead bodies define respective branches extending between the attachment point and the first and second target tissue sites.

The details of one or more embodiments of the invention are set forth in the accompanying drawings and the description below. Other features, objects, and advantages of the invention will be apparent from the description and drawings, and from the claims.

DETAILED DESCRIPTION

The invention relates to an assembly including at least two implantable medical elongated members that are coupled to each other via an attachment element. The elongated members each extend from a proximal end to a distal end. Each of the proximal ends are configured to be directly or indirectly coupled to an implantable or external medical device to deliver a therapy from the medical device to a respective target tissue site in a patient. The attachment element helps prevent the elongated members from unintentionally crossing over each other by fixing a position of a portion of the first elongated member with respect to a position of a portion of the second elongated member. Each of the elongated members defines a branch that extends from a most distally located attachment element to the respective distal ends of the elongated members. The branches are unattached and are generally movable with respect to each other.

Various embodiments of the elongated members may be applicable to different therapeutic applications. For example, one or more of the elongated members in the assembly may be a stimulation lead that is used to deliver electrical stimulation to a target stimulation site, a lead extension that connects to a lead to electrically connect the lead to a medical device or a connected lead and lead extension. In another embodiment, one or more of the elongated members may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient. In yet another embodiment, one or more of the elongated members may be a lead including one or more sensing electrodes to sense physiological parameters (e.g., blood pressure, temperature, cardiac activity, etc.) at a target tissue site within a patient. Thus, in some embodiments, "therapy" may include stimulation therapy, sensing or monitoring of one or more physiological parameters, fluid delivery, and the like. "Target tissue site" refers generally to the target site for implantation of an elongated member, regardless of the type of therapy. The invention is applicable to any configuration or type of implantable elongated members that are used to deliver therapy to sites in a patient. For purposes of illustration, however, the disclosure will refer to electrical stimulation leads.

Figure 1A:
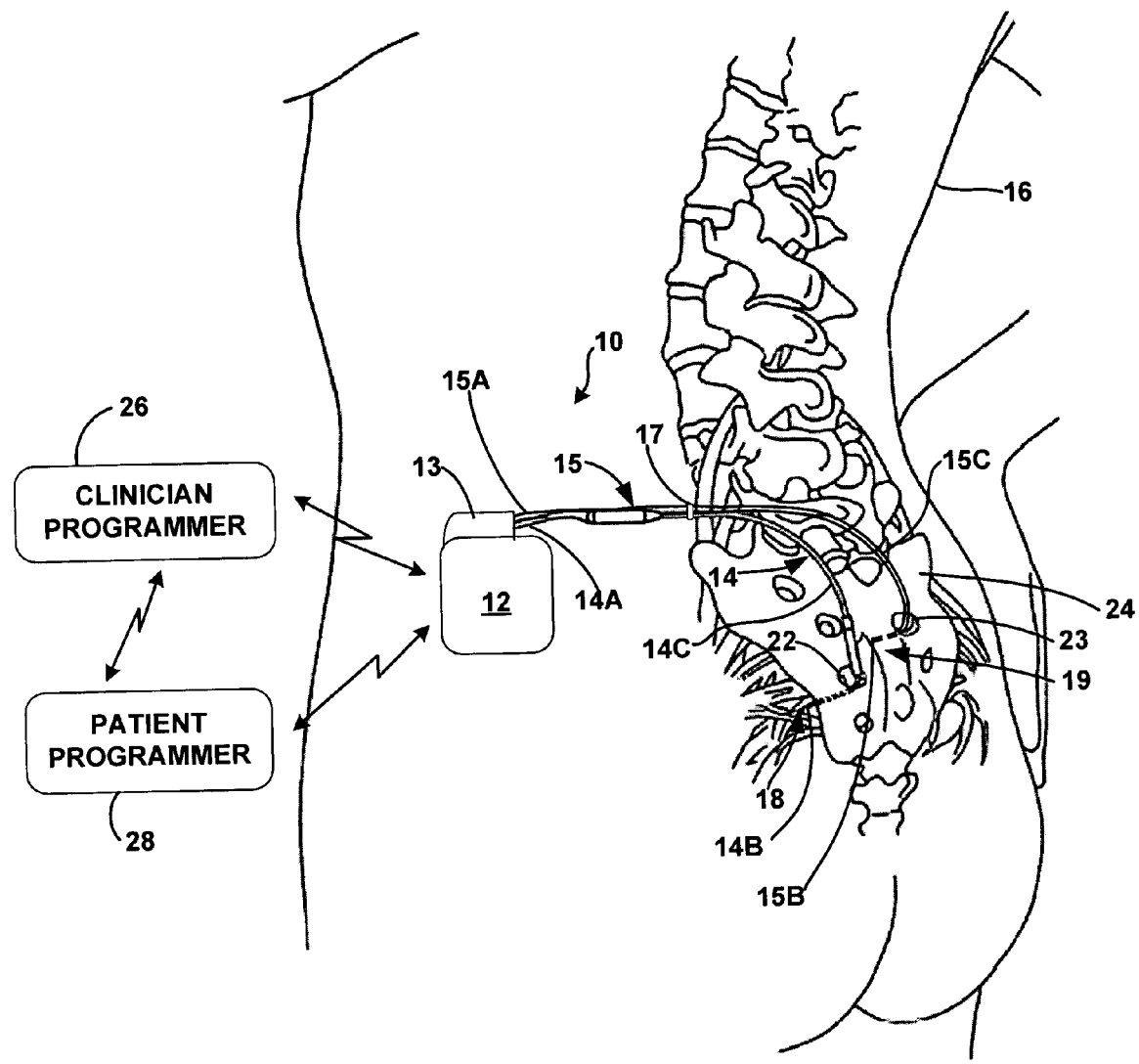
FIG. 1A is a schematic perspective view of a therapy system, which includes an electrical stimulator coupled to two implanted stimulation leads, which each have branches that have been implanted proximate to two target stimulation sites within a body of a patient.

FIG. 1A is a schematic perspective view of therapy system 10, which includes electrical stimulator 12 coupled to stimulation leads 14 and 15. Electrical stimulator 12 may be either implantable or external. In the example of FIG. 1A, electrical stimulator 12 has been implanted in a body of patient 16. For example, electrical stimulator 12 may be subcutaneously implanted in the body of a patient 16 (e.g., in a chest cavity, lower back, lower abdomen, or buttocks of patient 16 (not shown in FIG. 1A)). Electrical stimulator 12 provides a programmable stimulation signal (e.g., in the form of electrical pulses or substantially continuous-time signals) that is delivered to target stimulation sites 18 and 19 by implantable medical leads 14 and 15, respectively, and more particularly, via stimulation electrodes carried by leads 14 and 15. Electrical stimulator 12 may provide the same or a different signal to the electrodes of each of leads 14 and 15. Electrical stimulator 12 may also be referred to as a pulse or signal generator, and in the embodiment shown in FIG. 1A, electrical stimulator 12 may also be referred to as a neurostimulator. In some embodiments, lead 14 and/or lead 15 may also carry one or more sense electrodes to permit neurostimulator 12 to sense electrical signals or other physiological parameters from target stimulation site 18 and/or 19, respectively.

As described in greater detail below, at least one attachment element 17 is coupled to leads 14 and 15 such that a portion of lead 14 is held proximate to and in a fixed position with respect to a portion of lead 15. Proximal ends 14A and 15A of leads 14 and 15, respectively, may be both electrically and mechanically coupled to connector block 13 of neurostimulator 12 either directly or indirectly (e.g., via a lead extension). In particular, conductors disposed within the lead body of each of leads 14 and 15 may electrically connect stimulation electrodes (and sense electrodes, if present) adjacent to distal ends 14B and 15B of leads 14 and 15, respectively, to neurostimulator 12.

Leads 14 and 15 each define distal branches 14C and 15C, respectively, which extend from attachment element 17 to target stimulation sites 18 and 19, respectively. In the embodiment of therapy system 10 shown in FIG. 1A, branch 14C of lead 14 extends from attachment element 17 to target tissue site 18 such that distal end 14B of lead 14 is implanted and positioned within patient 16 to deliver electrically stimulation therapy to target stimulation site 18. Target tissue site 18 is proximate to the S3 sacral nerve. Lead 14 has been introduced into the S3 sacral foramen 22 of sacrum 24 to access the S3 sacral nerve. Branch 15C of lead 15 extends from attachment element 17 to target tissue site 19 such that distal end 15B of lead 15 is implanted and positioned within patient 16 to deliver electrical stimulation therapy to target stimulation site 19, which is proximate to the S2 sacral nerve. Lead 15 has been introduced into the S2 sacral foramen 23 of sacrum 24 to access the S2 sacral nerves.

Target stimulation sites 18 and 19 are separate from each other, and in some embodiments, may overlap. Although target stimulation sites 18 and 19 are shown in FIG. 1A as being different from each other, in other embodiments, target stimulation sites 18 and 19 may be the same, in which case branches 14C and 15C may be adjacent to each other. Regardless of the relative location of target stimulation sites 18 and 19 and the relative distance between branches 14C and 15C when leads 14 and 15 are implanted within patient 16, however, branches 14C and 15C of leads 14 and 15, respectively, are configured to deliver stimulation therapy to different sites 18 and 19 if desired because branches 14C and 15C are not attached and movable with respect to each other.

Figure 1B:
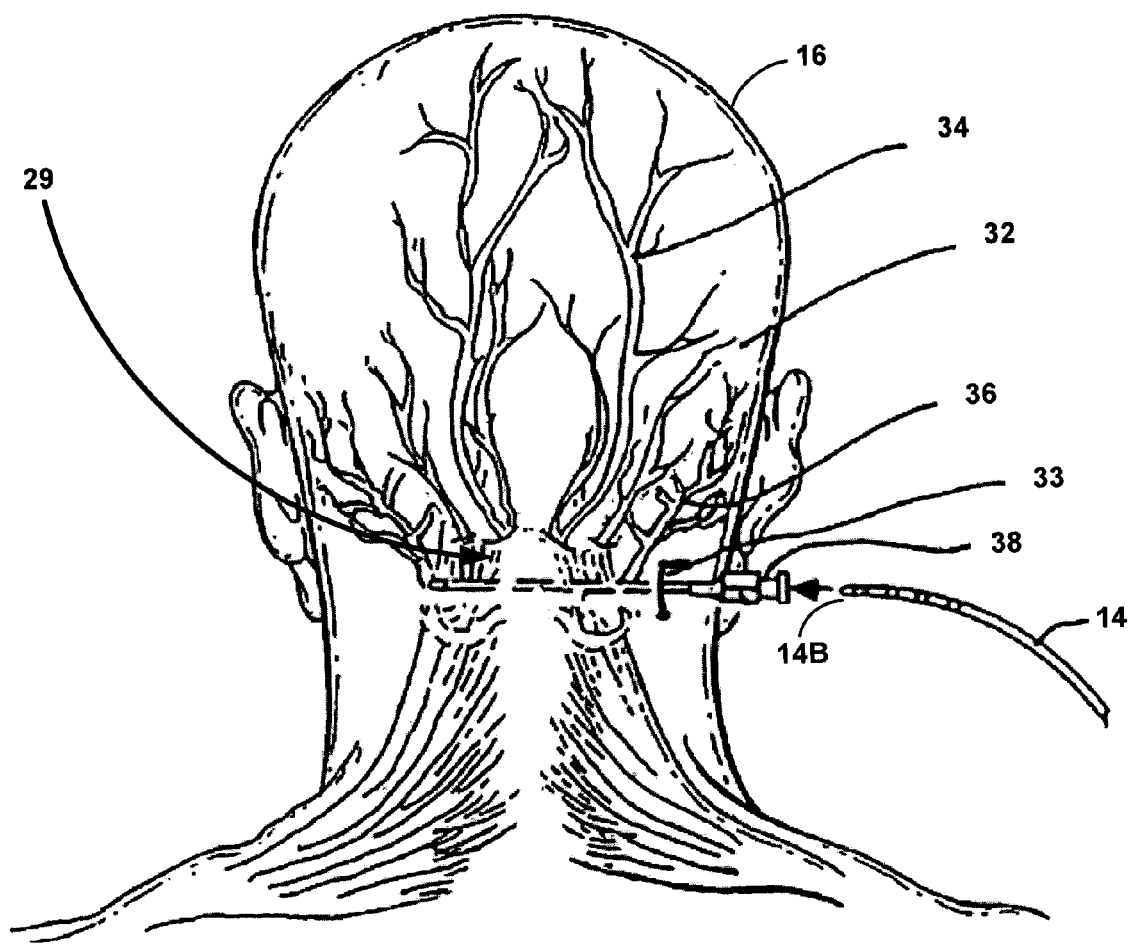
FIG. 1B illustrates the implantation of a stimulation lead at a location proximate to an occipital nerve.

Stimulation of the S2 and/or S3 sacral nerve may help treat pelvic floor disorders, urinary control disorders, fecal control disorders, interstitial cystitis, sexual dysfunction, and pelvic pain. Therapy system 10, however, is useful in other neurostimulation applications. Thus, in alternate embodiments, target stimulation sites 18 and 19 may be locations proximate to any of the other sacral nerves in patient 16 or any other suitable nerve in patient 16, which may be selected based on, for example, a therapy program selected for a particular patient. For example, in other embodiments, therapy system 10 may be used to deliver neurostimulation therapy to one or more pudendal nerve, one or more perineal nerves, one or more occipital nerves (as shown in FIG. 1B), or other areas of the nervous system, in which cases, leads 14 and 15 would be implanted proximate to the respective nerve.

Therapy system 10 also may include a clinician programmer 26 and a patient programmer 28. Clinician programmer 26 may be a handheld computing device that permits a clinician to program neurostimulation therapy for patient 16, e.g., using input keys and a display. For example, using clinician programmer 26, the clinician may specify neurostimulation parameters for use in delivery of neurostimulation therapy. Clinician programmer 26 supports telemetry (e.g., radio frequency telemetry) with neurostimulator 12 to download neurostimulation parameters and, optionally, upload operational or physiological data stored by neurostimulator 12. In this manner, the clinician may periodically interrogate neurostimulator 12 to evaluate efficacy and, if necessary, modify the stimulation parameters.

Like clinician programmer 26, patient programmer 28 may be a handheld computing device. Patient programmer 28 may also include a display and input keys to allow patient 16 to interact with patient programmer 28 and neurostimulator 12. In this manner, patient programmer 28 provides patient 16 with an interface for control of neurostimulation therapy by neurostimulator 12. For example, patient 16 may use patient programmer 28 to start, stop or adjust neurostimulation therapy. In particular, patient programmer 28 may permit patient 16 to adjust stimulation parameters such as duration, amplitude, pulse width and pulse rate, within an adjustment range specified by the clinician via clinician programmer 28, or select from a library of stored stimulation therapy programs.

Neurostimulator 12, clinician programmer 26, and patient programmer 28 may communicate via cables or a wireless communication, as shown in FIG. 1A. Clinician programmer 26 and patient programmer 28 may, for example, communicate via wireless communication with neurostimulator 12 using RF telemetry techniques known in the art. Clinician programmer 26 and patient programmer 28 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

As previously discussed, therapy system 10 may also be used to provide stimulation therapy to other nerves of a patient. For example, as shown in FIG. 1B, leads 14 and 15 (lead 15 is not shown in FIG. 1B) may be implanted proximate to an occipital region 29 of patient 16 for stimulation of one or more occipital nerves or a trigeminal nerve. In particular, leads 14 and 15 may be implanted proximate to lesser occipital nerve 32, greater occipital nerve 34, and third occipital nerve 36. Alternatively, leads 14 and 15 may be implanted proximate to the trigeminal nerve located on the side of the patient's head (not shown in FIG. 1B). In FIG. 1B, lead 14 is aligned to be introduced into introducer needle 38 and implanted proximate to occipital region 29 of patient 16 for stimulation of one or more occipital nerves 32, 34, and/or 36. A neurostimulator (e.g., neurostimulator 12 in FIG. 1A) may deliver stimulation therapy to any one or more of lesser occipital nerve 32, greater occipital nerve 34 or third occipital nerve 36 via electrodes disposed adjacent to distal ends 14B and 15B of leads 14 and 15. In alternate embodiments, leads 14 and 15 may be positioned proximate to one or more other peripheral nerves proximate to occipital nerves 32, 34, and 36 or a trigeminal nerve of patient 16, such as nerves branching from occipital nerves 32, 34, and 36 or the trigeminal nerve, as well as stimulation of any other suitable nerves throughout patient 16, such as, but not limited to, nerves within a brain, stomach or spinal cord of patient 16.

Implantation of lead 14, which is illustrated in FIG. 1B, may involve the subcutaneous placement of lead 14 transversely across one or more occipital nerves 32, 34, and/or 36 that are causing patient 16 to experience pain. In one example method of implanting lead 14 proximate to the occipital nerve, using local anesthesia, a vertical skin incision 33 approximately two centimeters (cm) in length is made in the neck of patient 16 lateral to the midline of the spine at the level of the C1 vertebra. The length of vertical skin incision 33 may vary depending on the particular patient. At this location, the skin and muscle of patient 16 are separated by a band of connective tissue referred to as fascia. Introducer needle 38 is introduced into the subcutaneous tissue, superficial to the fascia and muscle layer but below the skin. Occipital nerves 32, 34, and 36 are located within the cervical musculature and overlying fascia, and as a result, introducer needle 38 and, eventually, lead 14 are inserted superior to occipital nerves 32, 34, and 36.

Figure 3A:
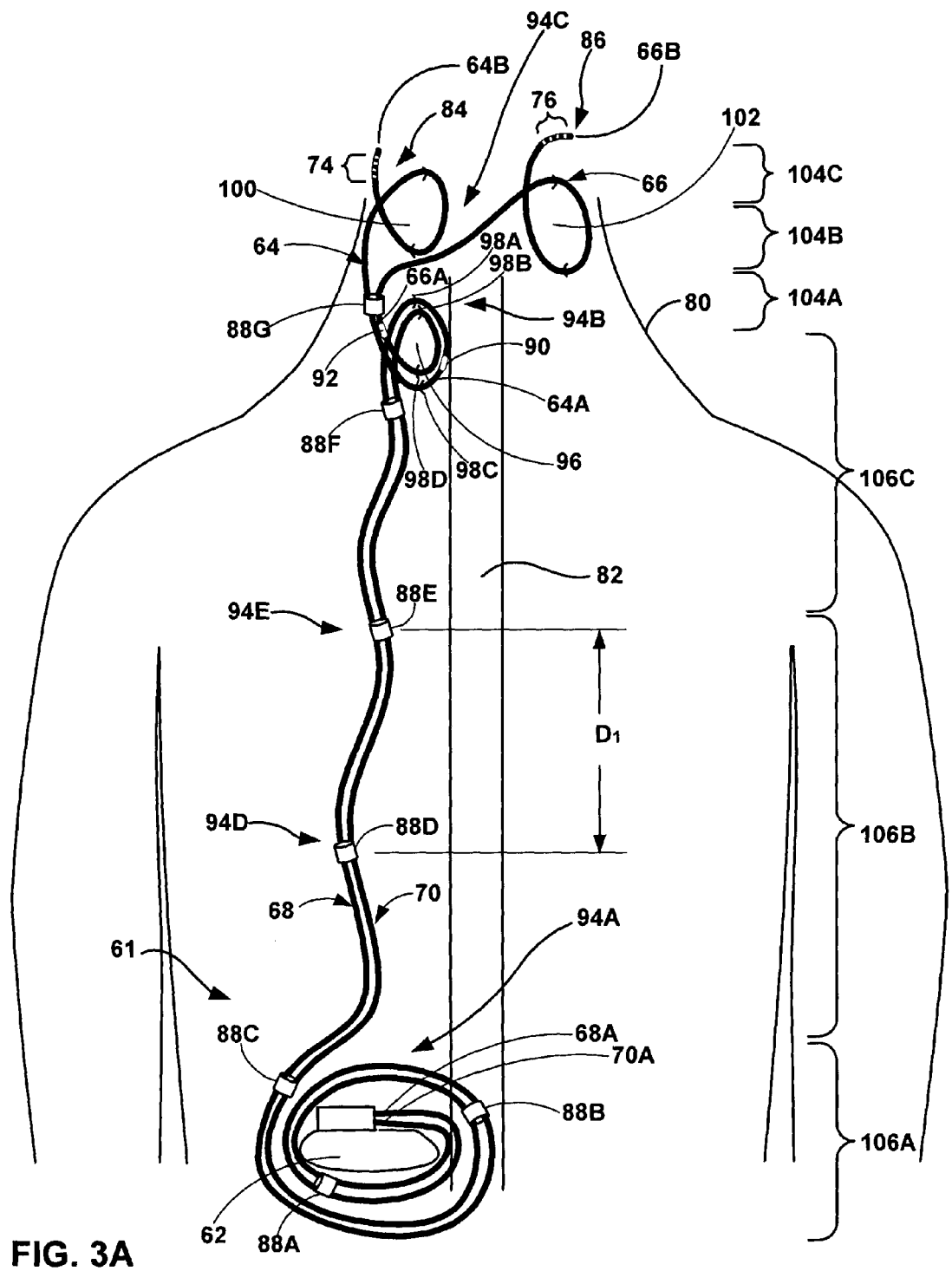
FIG. 3A is a schematic plan view of an electrical stimulation system including two leads and two lead extensions with attachment elements to help prevent crossover.
Figure 3B:
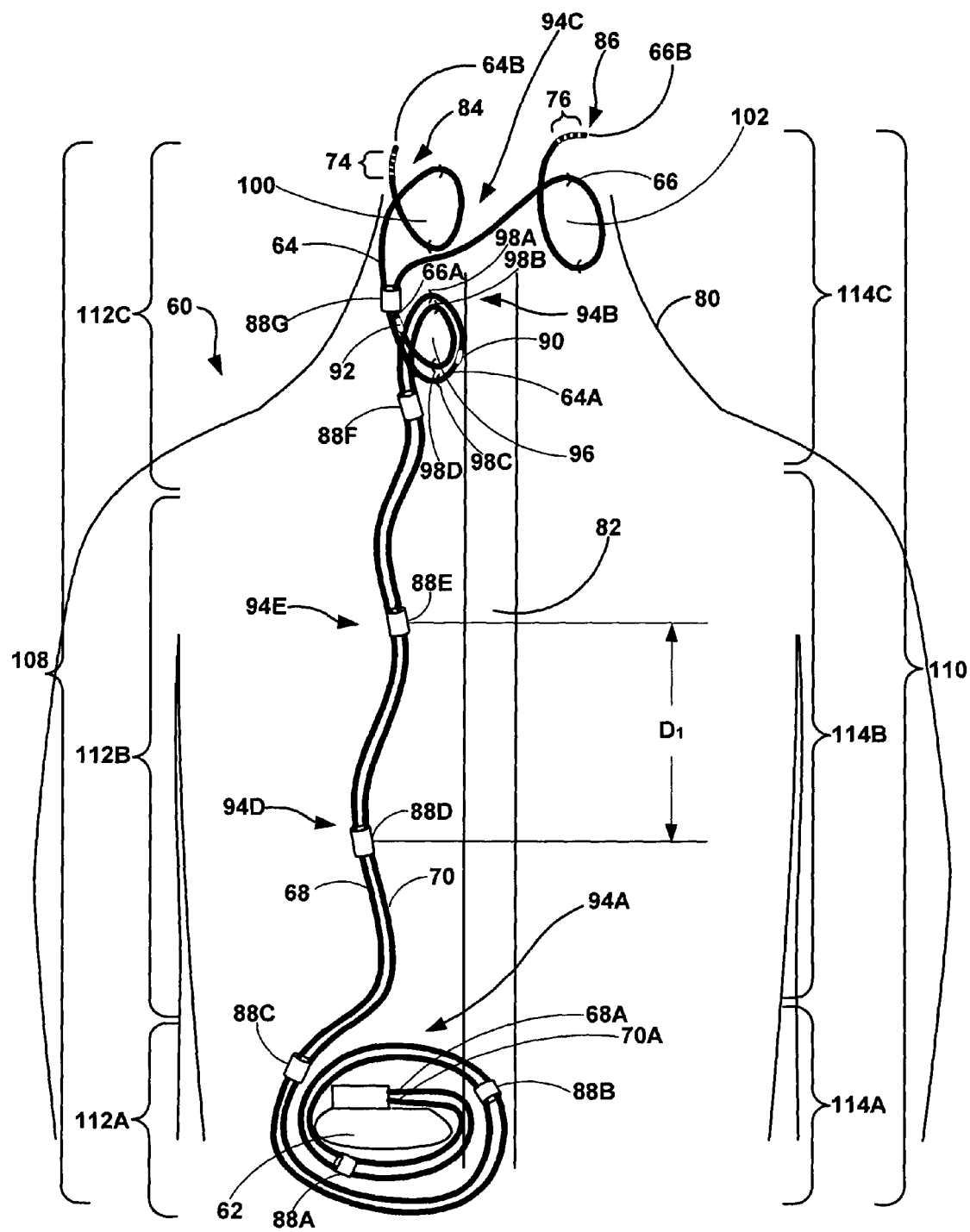
FIG. 3B is an alternative schematic plan view of the electrical stimulation system of FIG. 3A.
Figure 4:
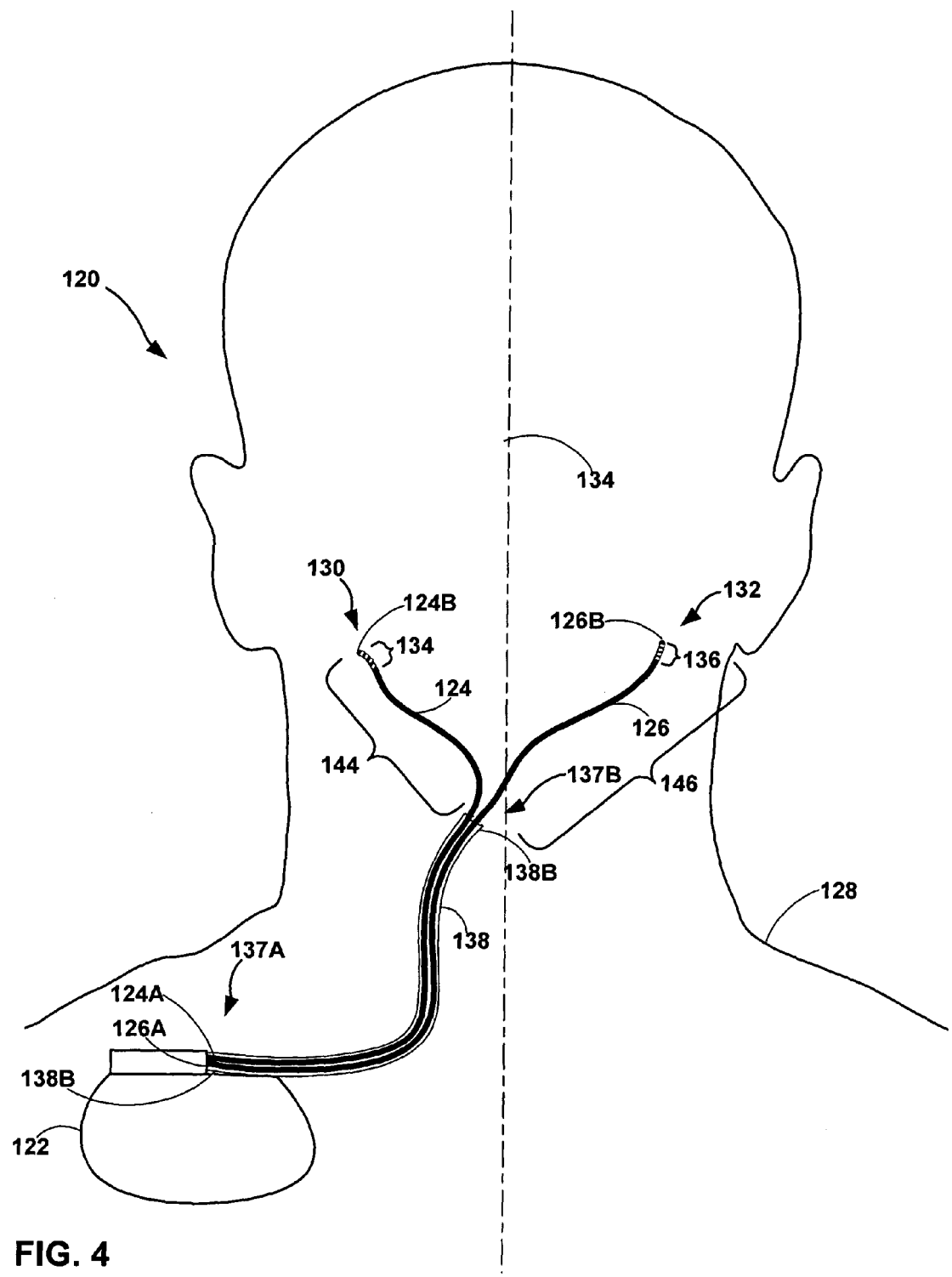
FIG. 4 is a schematic plan view of an electrical stimulation system including two leads that are attached to help prevent crossover.

Once introducer needle 38 is fully inserted, lead 14 may be advanced through introducer needle 38 and positioned to allow stimulation of the lesser occipital nerve 32, greater occipital nerve 34, third occipital nerve 36, and/or other peripheral nerves proximate to an occipital nerve. Upon placement of lead 14, introducer needle 38 may be removed. Lead 15 may be implanted using a procedure similar to the procedure used to implant lead 14. For example, lead 15 may be implanted using a needle introducer inserted through incision 33. The needle introducer used for lead 15 may or may not be the same as needle introducer 38 used for lead 14. As shown in FIGS. 3A-4, leads 14 and 15 may be positioned within patient 16 such that distal ends 14A and 15A of leads 14 and 15, respectively, are located on opposite sides of a midline of patient 16. Such an arrangement of leads 14 and 15 may be useful for achieving bilateral stimulation of occipital region 29 of patient 16. In general, bilateral stimulation includes stimulation of two regions of a patient either sequentially or simultaneously. The two regions are typically on opposite sides of a midline of patient 16, and typically include two branches of a nerve. Bilateral stimulation may include, for example, stimulation of two branches of occipital nerves 32, 34, 36 or the trigeminal nerve that are on opposite sides of the head of patient 16.

An electrical stimulator (e.g., neurostimulator 12 in FIG. 1A) that is used to deliver therapy to patient 16 via leads 14 and 15 may be implanted at any suitable location within patient 16, e.g., above the trapezius muscle, near the clavicle, shoulder, abdomen, buttock, etc. If the electrical stimulator is implanted at a location of substantial distance from the target tissue site (e.g., target stimulation sites 18 and 19 of FIG. 1A or occipital region 29 of FIG. 1B), the length of leads 14 and 15 may be relatively long in order to extend between the electrical stimulator and the target tissue site. The relatively long leads 14 and 15 may, for example, traverse from an abdomen or chest cavity of patient 16 to occipital region 29.

Regardless of the actual distance traversed by leads 14 and 15, it may be desirable to attach lead 14 to lead 15 at one or more points proximal to the target stimulation sites to define distal branches 14C and 15C that are separable from each other. While leads 14 and 15 do not necessarily need to be abutted together, attaching at least one portion of leads 14 and 15 together may help prevent unintentional cross-over between leads 14 and 15. If leads 14 and 15 unintentionally cross-over each other at one or more points between neurostimulator 12 and the target tissue site, leads 14 and 15 may be effectively shortened, which may result in migration of leads 14 and 15. As described with reference to FIG. 5A, in some cases, it may be desirable to intentionally cross leads 14 and 15. In such an embodiment, it may be desirable to maintain the intentional cross-over arrangement between leads 14 and 15 by attaching leads 14 and 15.

Accurate lead placement may affect the success of electrical stimulation therapy. For example, with respect to occipital nerve stimulation (FIG. 1B), if lead 14 and/or lead 15 is located too deep, i.e., anterior, in the subcutaneous tissue, patient 16 may experience muscle contractions, grabbing sensations, or burning. Such problems may additionally occur if lead 14 and/or lead 15 migrates after implantation. Furthermore, due to the location of implanted leads 14 and 15 in the neck of patient 16, leads 14 and 15 may be subjected to pulling and stretching that may increase the chances of lead migration and may also increase the possibility of cross-over between leads 14 and 15. For these reasons, leads 14 and 15 are fixed together by attachment element 17.

Leads 14 and 15 may also include one or more fixation elements that engage with surrounding tissue to help prevent migration. Examples of actively or passively deployed fixation elements include, but are not limited to, one or more tines, barbs, hooks, wire-like elements, adhesives (e.g., surgical adhesives), balloon-like fixation elements, collapsible or expandable fixation structures, tissue-receiving cavities, and so forth. The fixation elements may be, for example, located proximate to the electrodes (shown in FIG. 2A) of leads 14 and 15. The fixation elements may be composed of any suitable biocompatible material, including, but not limited to, titanium, stainless steel, Nitinol, other shape memory materials, hydrogel or combinations thereof.

In alternate applications of leads 14 and 15, target stimulation sites 18 and 19 may be at a location proximate to any of the other sacral nerves in patient 16 or any other suitable nerve, organ, muscle, muscle group, or other tissue site in patient 16, which may be selected based on, for example, a therapy program selected for a particular patient. For example, therapy system 10 may be used to deliver electrical stimulation therapy to one or more pudendal nerve, one or more perineal nerve, or other areas of the nervous system, in which cases, leads 14 and 15 would be implanted proximate to the respective nerve(s). As further examples, leads 14 and 15 may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders. Accordingly, although patient 16 and occipital region 29 of FIG. 1B are referenced throughout the remainder of the disclosure for purposes of illustration, electrical stimulation leads 14 and 15 in accordance with the invention may be adapted for use in a variety of electrical stimulation applications, including sacral nerve stimulation, as shown in FIG. 1A with respect to target stimulation sites 18 and 19.

Figure 2A:
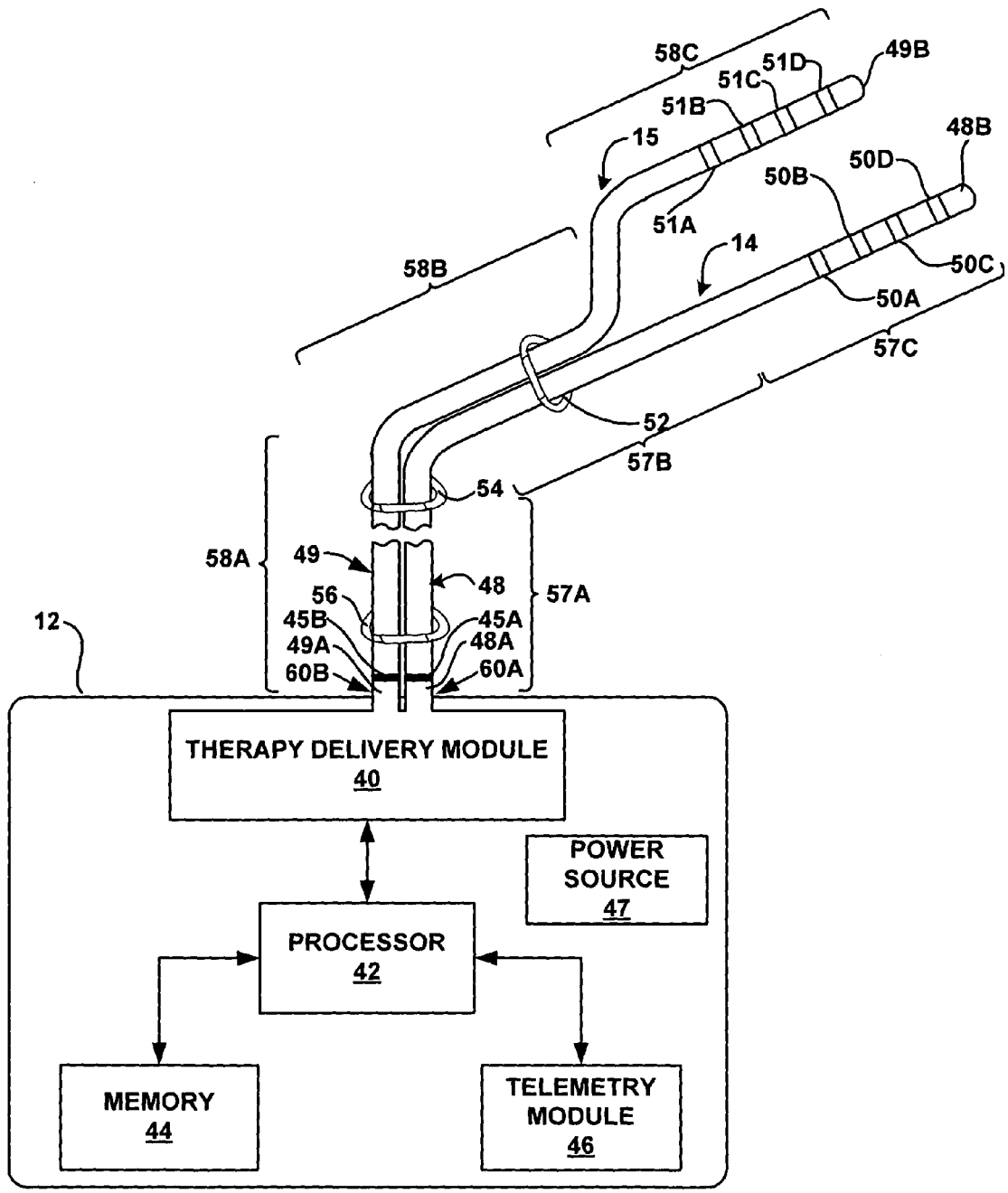
FIG. 2A is a schematic block diagram illustrating various components of an electrical stimulator and two implantable leads.

FIG. 2A is a block diagram illustrating various components of neurostimulator 12 and implantable leads 14 and 15. Neurostimulator 12 includes therapy delivery module 40, processor 42, memory 44, telemetry module 46, and power source 47. In some embodiments, neurostimulator 12 may also include a sensing circuit (not shown in FIG. 2A). Implantable lead 14 includes lead body 48 extending between proximal end 48A and distal end 48B. Similarly, implantable lead 15 includes lead body 49 extending between proximal end 49A and distal end 49B. Lead bodies 48 and 49 may be cylindrical or may be paddle-shaped (i.e., a "paddle" lead).

Electrodes 50A, 50B, 50C, and 50D (collectively "electrodes 50") are disposed on lead body 48 adjacent to distal end 48B of lead body 48. Electrodes 51A, 51B, 51C, and 51D (collectively "electrodes 51") are disposed on lead body 49 adjacent to distal end 49B of lead body 49. The configuration, type, and number of electrodes 50 and 51 illustrated in FIG. 2A are merely exemplary. In some embodiments, electrodes 50 and 51 may be ring electrodes. In other embodiments, electrodes 50 and 51 may be segmented or partial ring electrodes, each of which extends along an arc less than 360 degrees (e.g., 90-120 degrees) around the periphery of lead bodies 48 and 49, respectively.

In embodiments in which lead 14 is a paddle lead, electrodes 50 may extend along one side of lead body 48. Electrodes 50 extending around a portion of the circumference of lead body 48 or along one side of a paddle lead may be useful for providing an electrical stimulation field in a particular direction/targeting a particular therapy deliver site. For example, in the electrical stimulation application shown in FIG. 1B, electrodes 50 may be disposed along lead body 48 such that the electrodes face toward occipital nerves 32, 34, and/or 36, or otherwise away from the scalp of patient 16. This may be an efficient use of stimulation because electrical stimulation of the scalp may not provide any or may provide minimal useful therapy to patient 16. In addition, the use of segmented or partial ring electrodes 50 may also reduce the overall power delivered to electrodes 50 by neurostimulator 12 because of the efficient delivery of stimulation to occipital nerves 32, 34, and/or 36 (or another target stimulation site) by eliminating or minimizing the delivery of stimulation to unwanted or unnecessary regions within patient 16. Electrodes 51 of lead 15 may also incorporate the structural features described with respect to electrodes 50 and lead 14.

In embodiments in which electrodes 50 extend around a portion of the circumference of lead body 48 or along one side of a paddle lead, lead 14 may include one or more orientation markers 45A proximate to proximal end 14A that indicate the relative location of electrodes 50. Orientation marker 45A may be a printed marking on lead body 48, an indentation in lead body 48, a radiographic marker, or another type of marker that is visible or otherwise detectable (e.g., detectable by a radiographic device) by a clinician. Orientation marker 45A may help a clinician properly orient lead 14 such that electrodes 50 face the desired direction (e.g., toward occipital nerves 32, 34, and/or 36) within the patient. For example, orientation marker 45A may also extend around the same portion of the circumference of lead body 48 or along the side of the paddle lead as electrodes 50. In this way, orientation marker 45A faces the same direction as electrodes 50, thus indicating the orientation of electrodes 50 to the clinician. When the clinician implants lead 14 in the patient, orientation marker 45A may remain visible to the clinician. Lead 15 may also include one or more orientation markers 45B to indicate a direction of electrodes 51.

Neurostimulator 12 delivers stimulation therapy via electrodes 50 and 51 of leads 14 and 15. Electrodes 50 and 51 are electrically coupled to a therapy delivery module 40 of neurostimulator 12 via conductors within lead bodies 48 and 49, respectively. The conductors are separated from each other via an electrically insulating material. In some embodiments, the outer surface of lead bodies 48 and 49 are formed at least in part of the electrically insulating material. Proximal end 48A of lead body 48 includes contacts (not shown) to electrically couple electrodes 50 directly to neurostimulator 12 or indirectly to neurostimulator 12 (e.g., via a lead extension). Similarly, proximal end 49A of lead body 49 includes contacts (not shown to electrically couple electrodes 51 directly to neurostimulator 12 or indirectly to neurostimulator 12 (e.g., via a lead extension). In one embodiment, an implantable signal generator or other stimulation circuitry within therapy delivery module 40 delivers electrical signals (e.g., pulses or substantially continuous-time signals, such as sinusoidal signals) to target stimulation sites 18 and 19 (FIG. 1A) via at least some of electrodes 50 and 51 under the control of a processor 42.

Neurostimulator 12 includes two connection ports 60A and 60B that are each configured to receive one of leads 14 and 15 (or a lead extension, if used). Connection ports 60A and 60B are configured to support (i.e., electrically connect to) a limited number of electrodes. In the embodiment shown in FIG. 2A, connection ports 60A and 60B are each configured to support eight electrodes. By utilizing both connection ports 60A and 60B, the number of stimulation/sense electrodes are maximized. That is, because two leads 14 and 15 are coupled to separate connection ports 60A and 60B of neurostimulator 12, leads 14 and 15 may each carry a greater number of electrodes while still providing bifurcated-like branches 14C and 15C (described in further detail with reference to FIG. 2B) as compared to a single bifurcated lead connected to a single connection port 60A or 60B of neurostimulator 12. Neurostimulator 12 may provide a greater range of electrical signals to target stimulation sites 18 and 19 as compared to a neurostimulator coupled to a single lead because two leads 14 and 15 support a greater number of electrode combinations and increases the number of independently activatable electrodes. In addition, use of two separate leads 14 and 15 may also enable processor 42 to selectively deliver stimulation to one lead 14 or 15, which may be positioned at separate target stimulation sites 18 and 19, respectively.

The implantable signal generator may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power.

The stimulation energy generated by therapy delivery module 40 may be formulated as neurostimulation energy, e.g., for treatment of any of a variety of neurological disorders, or disorders influenced by patient neurological response. The signals may be delivered from therapy delivery module 40 to electrodes 50 and 51 via a switch matrix and conductors carried by leads 14 and 15 and electrically coupled to respective electrodes 50 and 51.

Processor 42 may include a microprocessor, a controller, a DSP, an ASIC, an FPGA, discrete logic circuitry, or the like. Processor 42 controls the implantable signal generator within therapy delivery module 40 to deliver neurostimulation therapy according to selected stimulation parameters. Specifically, processor 42 controls therapy delivery module 40 to deliver electrical signals with selected amplitudes, pulse widths (if applicable), and rates specified by the programs. In addition, processor 42 may also control therapy delivery module 40 to deliver the neurostimulation signals via selected subsets of electrodes 50 or 51 with selected polarities. For example, electrodes 50 may be combined in various bipolar or multi-polar combinations to deliver stimulation energy to selected sites, such as nerve sites adjacent the spinal column, pelvic floor nerve sites, or cranial nerve sites. Electrodes 51 may also be combined in various bipolar or multi-polar combinations to deliver stimulation energy to selected sites, such as nerve sites adjacent the spinal column, pelvic floor nerve sites, or cranial nerve sites.

Processor 42 may also control therapy delivery module 40 to deliver each signal according to a different program, thereby interleaving programs to simultaneously treat different symptoms or provide a combined therapeutic effect. For example, in addition to treatment of one symptom such as sexual dysfunction, neurostimulator 12 may be configured to deliver neurostimulation therapy to treat other symptoms such as pain or incontinence.

Memory 44 of neurostimulator 12 may include any volatile or non-volatile media, such as a RAM, ROM, NVRAM, EEPROM, flash memory, and the like. In some embodiments, memory 44 of neurostimulator 12 may store multiple sets of stimulation parameters that are available to be selected by patient 16 via patient programmer 28 (FIG. 1) or a clinician via clinician programmer 26 (FIG. 1) for delivery of neurostimulation therapy. For example, memory 44 may store stimulation parameters transmitted by clinician programmer 26 (FIG. 1). Memory 44 also stores program instructions that, when executed by processor 42, cause neurostimulator 12 to deliver neurostimulation therapy. Accordingly, computer-readable media storing instructions may be provided to cause processor 42 to provide functionality as described herein.

In particular, processor 42 controls telemetry module 46 to exchange information with an external programmer, such as clinician programmer 26 and/or patient programmer 28 (FIG. 1), by wireless telemetry. In addition, in some embodiments, telemetry module 46 supports wireless communication with one or more wireless sensors that sense physiological signals and transmit the signals to neurostimulator 12.

Crossover of leads 14 and 15, i.e., lead body 48 crossing under or over lead body 49 at one of more locations, may be undesirable, and may have detrimental effects on the quality of therapy delivered to patient 16 and/or may cause patient discomfort. For example, at crossover locations, lead bodies 48 and 49 may experience increased rubbing, which may cause wear-through or damage to lead bodies 48 and 49. Erosion of the outer surfaces of lead bodies 48 and 49 may, for example, result in exposure of the electrical conductors that are disposed within lead bodies 48 and 49. In applications in which leads 14 and 15 are implanted in subcutaneous tissue, e.g., in occipital or trigeminal nerve stimulation applications, visible bulges in the patient's skin may occur at crossover points. In addition to being aesthetically displeasing, bulges may cause patient discomfort. Furthermore, crossover may increase the strain on leads 14 and 15, by effectively shortening leads 14 and 15, which may result in increased pulling of on leads 14 and 15 as patient 16 moves.

To that end, attachment elements 52, 54, and 56 are coupled to lead bodies 48 and 49 to help prevent crossover by fixing the relative distance between portions of lead 14 proximate to lead 15. Attachment elements 52, 54, and 56 do not necessarily hold lead bodies 48 and 49 at a fixed distance with respect to each other, but rather, in some embodiments, attachment elements 52, 54, and 56 may be flexible, enabling some relative movement between lead bodies 48 and 49. In general, however, attachment elements 52, 54, and 56 aid in keeping lead 14 oriented on one side of lead 15 such that lead bodies 48 and 49 do not cross. In some embodiments, attachment elements 52, 54, and 56 also help prevent contact between lead bodies 48 and 49 at each of the locations of attachment elements 52, 54, and 56. Additionally, attachment elements 52, 54, and 56 may simplify implantation of leads 14 and 15 by aiding in lead management.

In the embodiment shown in FIG. 2A, attachment elements 52, 54 and 56 do not require sutures to hold lead bodies 48 and 49 together, and therefore may be referred to as sutureless attachment elements. Of course, sutures may be used if desired. Sutureless attachment elements may be less invasive and require less application time and thereby a shorter overall operation time compared to sutures. Attachment elements 52, 54 and 56 are shown to be clip-like structures in FIG. 2A. In one embodiment, clip-like attachment structures may be laterally attached or removed from lead bodies 48, 49, which may help eliminate the need to advance attachment elements 52, 54, and 56 from a proximal end 48A, 49A or distal end 48B, 49B of each lead body 48, 49. In some embodiments, clip-like attachment elements structures 52, 54 and 56 may each be moveable between an open and closed position, and may each include a mechanism for fixing the clips in the closed position. In the closed position, clip-like attachment elements 52, 54, and 56 engage with each lead body 48 and 49 in order to remain substantially fixed to lead bodies 48 and 49 (e.g., to prevent sliding along lead bodies 48 and 49). For example, clip-like attachment elements 52, 54, and 56 may friction fit with an outer surface of lead bodies 48 and 49, or may include a sharp element that "bites" into the outer surface of lead bodies 48 and 49. One or more of attachment elements 52, 54 and 56 may be at least partially composed of silicone or other suitable polymers.

In other embodiments, attachment elements 52, 54 and 56 may be any suitable attachment element. For example, one or more of attachment elements 52, 54, and 56 may be adhesive elements such as fibrin glue, 2-octyl cyanoacrylate, epoxy, silicone, polymers with melting points higher than 37 degrees Celsius, e.g., a derivative of polypropylene or polyethylene, or other suitable types of biocompatible adhesives. In other embodiments, attachment elements 52, 54 and 56 may be sheaths. Sheath attachment elements may require axial insertion of leads along the longitudinal axis of the sheaths or may be wrapped around the leads and secured with a connector feature, e.g., an adhesive strip or interlocking feature. An example of a sheath element is shown in FIG. 4.

Lead 14 includes proximal section 57A adjacent to proximal end 48A, distal section 57C adjacent to distal end 48B, and middle section 57B located between proximal section 57A and distal section 57C. Proximal section 57A, middle section 57B, and distal section 57C have approximately equal lengths. Similarly, lead 15 includes proximal section 58A, middle section 58B, and distal section 58C. Proximal section 58A, middle section 58B, and distal section 58C have approximately equal lengths. Attachment element 52 is coupled to middle sections 57B and 58B of leads 14 and 15, respectively. Attachment elements 54 and 56 are coupled to proximal sections 57A and 58A of leads 14 and 15, respectively. In FIG. 2A, distal sections 57C and 58C are shown unattached. However, in some embodiments, distal sections 57C and 58C may also include one or more attachment element proximal to electrodes 50 and 51 that attach to portions of distal sections 57C and 58C such that distal ends 48B and 49B of leads 14 and 15 and electrodes 50 and 51 remain unattached. Otherwise stated, in some embodiments, distal sections 57C and 58C of lead bodies 48 and 49, respectively, may be attached via an attachment element so long as lead bodies 48 and 49 define separate and separable branches 14C and 15C (shown in FIG. 2B) that may be implanted at different target tissue sites within patient 16.

Figure 2B:
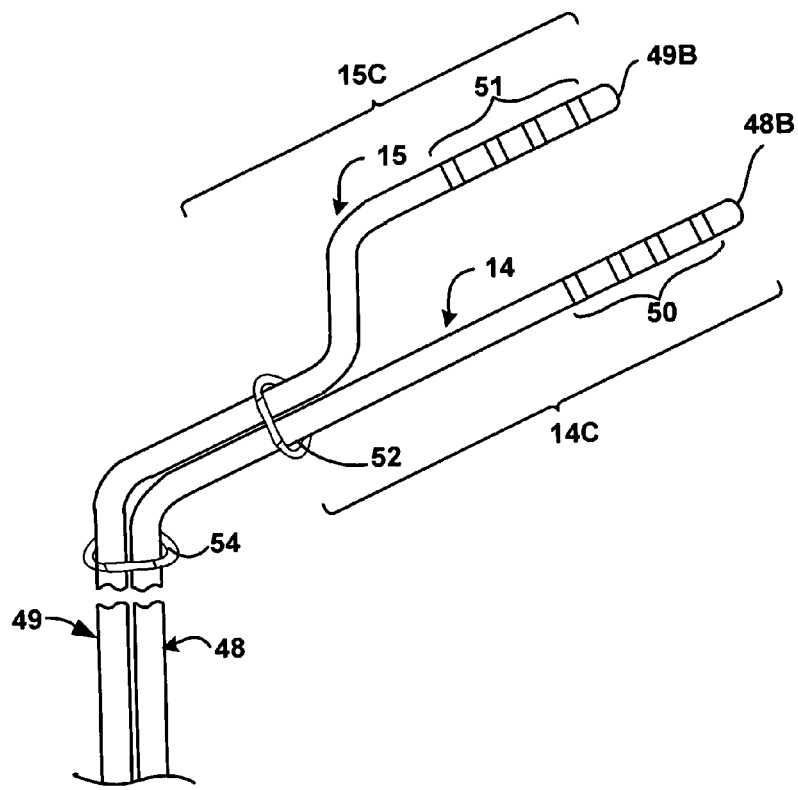
FIG. 2B illustrates the implantable leads shown in FIG. 2A.

FIG. 2B illustrates leads 14 and 15 shown in FIG. 2A. When leads 14 and 15 are attached together at one or more points, leads 14 and 15 define unattached branches 14C and 15C, respectively, proximate to the distal end 48B and 49B of the respective lead bodies 48 and 49. In the embodiment shown in FIGS. 2A and 2B, lead body 48 defines branch 14C that extends from a most distal attachment element 52 to distal end 48B of lead body 48, while lead body 49 defines branch 15C that extends from a most distal attachment element 52 to distal end 49B of lead body 48. Each of the branches are substantially equal in length.

Figure 2C:
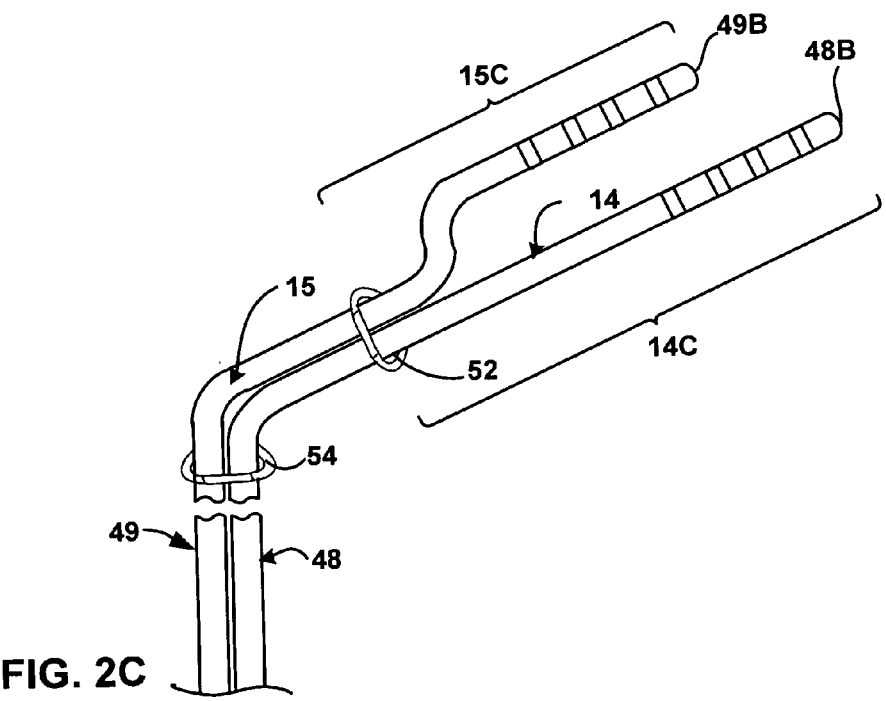
FIG. 2C illustrates the implantable leads shown in FIGS. 2A and 2B that define branches having different lengths.

In other embodiments, as shown in FIG. 2C, branches 14C and 15C may have different lengths. Different length branches 14C and 15C may be achieved by any suitable method. For example, lead bodies 48 and 49 may have different lengths or attachment element 52 may be positioned askew with respect to distal ends 48B and 49B of lead bodies 48 and 49, respectively, such that branches 14C and 15C have different lengths. Lead branches 14C and 15C may also have different lengths of distal ends 48B and 49B of lead bodies 48 and 49, respectively, are otherwise unaligned when attached together. Different length branches 14C and 15C may be useful for providing stimulation therapy to two different target stimulation sites 18 and 19 that are not equidistant from the implant site of neurostimulator 12.

FIG. 3A is a schematic plan view of therapy system 61, which includes neurostimulator 62 coupled to neurostimulation leads 64 and 66 via lead extensions 68 and 70, respectively. Leads 64 and 66 are positioned for stimulation of an occipital region (e.g., occipital region 29 in FIG. 1B) of patient 80. Lead 64 extends from proximal end 64A to distal end 64B and includes electrodes 74 proximate to distal end 64B, and lead extension 68 extends from proximal end 68A to distal end 68B. Similarly, lead 66 extends from proximal end 66A to distal end 66B and includes electrodes 76 proximate to distal end 66B, and lead extension 68 extends from proximal end 68A to distal end 68B. In the illustrated embodiment, leads 64 and 66 and lead extensions 68 and 70 are implanted in a back of patient 80 such that leads 64 and 66 and lead extensions 68 and 70 run substantially parallel to spinal cord 82.

Leads 64 and 66 deliver electrical stimulation therapy to (or sense parameters from) target tissue sites 84 and 86, respectively, via electrodes 74 and 76, respectively. Target tissue sites 84 and 86 may be located on opposite sides of the patient's midline. In the illustrated embodiment, the midline of patient 80 is represented by spinal cord 82 and divides patient 80 into approximately equal and symmetrical left and right halves. To help facilitate the delivery of therapy to two target stimulation sites 84 and 86 from leads 64 and 66, distal ends 64B and 66B of leads 64 and 66 are separated and unattached from each other. Additionally, electrodes 74 and 76 carried by leads 64 and 66 may be unattached and separable from each other, which enables electrodes 74 and 76 to support bilateral stimulation of target stimulation sites 84 and 86.

In one embodiment, at least a portion of neurostimulation lead 64 may include radio-opaque material that is detectable by imaging techniques, such as fluoroscopic imaging or x-ray imaging. This feature may be helpful for maneuvering neurostimulation lead 64 relative to target tissue site 84 when implanting lead 64 within patient 80. For example, the distal end 64B of neurostimulation lead 64 may include radio-opaque material that is visible via fluoroscopic imaging. Radio-opaque markers, as well as other types of markers, such as other types of radiographic and/or visible markers, may also be employed to assist a clinician during the introduction and withdrawal of neurostimulation lead 64 from patient 68. Additionally lead 66, lead extension 68 and/or lead extension 70 may include markers to aid implantation and/or explantation, as described with respect to lead 64. For example, fixation elements and/or attachment points on lead 64, lead 66, lead extension 68, and/or lead extension 70 may include radio-opaque markers to assist in locating fixation elements and/or attachment points, which may be useful if lead 64 is removed or repositioned.

Proximal ends 68A and 70A of lead extensions 68 and 70, respectively, are coupled to neurostimulator 62, which is implanted in the abdomen of patient 80, and distal ends 64B and 66B of leads 64 and 66 are implanted proximate to target tissue sites 84 and 86, respectively, in the neck of patient 80. Proximal end 68A of lead extension 68 may include a first group of electrical contacts that directly electrically connect to neurostimulator 62. The first group of electrical contacts on lead extension 68 are configured to electrically connect to electrodes 74 on lead 64 via another group of electrical contacts on distal end 68B lead extension 68 that are configured to electrically connect with a third group of electrical contacts on proximal end 64A of lead 64. For example, one electrical contact on lead extension 68 contacts one electrical contact on lead 64. Each of the electrical contacts of the third group may be electrically connected to electrodes 74 via electrical conductors disposed within lead 64. The electrical conductors are typically electrically insulated from each other such that a separate signal may be sent to each electrode 74, if desired.

Lead extension 70 may be electrically connected to electrodes 76 of lead 66 via a similar set of electrical contacts. For example, proximal end 70A of lead extension 70 may include a group of electrical contacts that electrically connect directly to neurostimulator 62. Distal end 70B of lead extension 70 may include another group of electrical contacts that electrically connect to a respective group of electrical contacts on proximal end 66A of lead 66. Each of the electrical contacts on proximal end 66A of lead 66 may be electrically connected to one of electrodes 76 via electrical conductors disposed within lead 66.

Lead 64 and lead extension 68 are coupled together using connector 90 at incision site 94B. Similarly, lead 66 and lead extension 70 are coupled together using connector 92 at incision site 94B. A clinician may make a relatively small incision at incision site 94B, such as an incision about two centimeters (cm) to about five cm long, and couple lead 64 to lead extension 68, and couple lead 66 to lead extension 70 and create strain relief loop 96. Leads 64 and 66 may be tunneled to incision site 94B from target tissue sites 84 and 86, respectively. Alternatively, leads 64 and 66 may be tunneled from incision site 94C up to the respective target tissue site 84 and 86. Strain relief loop 96 may be located proximate to connectors 90 and 92.

Strain relief loop 96 may be formed by suturing one or more portion of leads 64 and 66 and/or lead extensions 68 and 70 to patient 80. More specifically, in the illustrated embodiment, sutures 98A-98D are loosely placed over lead extension 68, lead extension 70, lead 64, and lead 66, respectively, around strain relief loop 96. In other embodiments, a greater or fewer number of sutures may be used. For example, in one embodiment, a single suture may be used instead of sutures 98A and 98B. Sutures 98A-98D are loosely disposed around leads 64, 66 and lead extensions 68, 70 to allow the portions of the elongated bodies (e.g., leads 64 and 66 and lead extensions 68 and 70) which sutures 98A-98D contact to slide beneath sutures 98A-98D if strain relief is needed. For example, if lead extension 68 and/or 70 experiences tension, strain relief loop 96 may allow extension 68 and/or 70 to temporary lengthen. Other suitable methods of forming strain relief loop 96 may also be used. In addition, strain relief loop 96 may be reduced in size or eliminated in some embodiments, such as when lead bodies 48 and 49 include elastic portions that are stretchable to temporarily elongate lead bodies 48 and 49.

Additionally, multiple strain relief loops may be used along the length of leads 64 and 66 and/or lead extensions 68 and 70. For example, strain relief loops 100 and 102 are formed on leads 64 and 66, respectively. However, since forming a strain relief loop typically requires an incision, it may be desirable to limit the use of strain relief loops to incision sites 94A-94E in order to minimize the invasiveness of the lead implantation procedure. In the embodiment shown in FIG. 3A, strain relief loops 96, 100, and 102 are formed at incision sites 94A-94E that also serve another purpose, and therefore, are used in the implantation technique regardless of whether strain relief loops 96, 100 or 102 are formed. Accordingly, the invasiveness of the lead implantation procedure is not further complicated by forming strain relief loops 96, 100, and 102. For example, incision site 94B is where an incision is made to couple lead 64 with lead extension 68 and lead 66 with lead extension 70. Incision site 94C is where an incision is made to properly, place distal ends 64B and 66B of leads 64 and 66 at target tissue sites 84 and 86, respectively. Additionally, an incision is made at incision site 94A to implanted neurostimulator 62 and couple lead extensions 68 and 70 to neurostimulator 62. Proximate to incision site 94A, lead extensions 68 and 70 are shown looped around neurostimulator 62, which also provides strain relief.

Incisions may be made along the length of lead extensions 68 and 70 at incision sites 94D and 94E. In one embodiment, leads 64 and 66 are tunneled individually from incision site 94C to their respective target tissue sites 84 and 86. Leads 64 and 66 may be tunneled individually or together from incision site 94C to incision site 94B. From incision site 94B, lead extensions 68 and 70 may be tunneled together using a tunneling tool that creates a path large enough for both lead extensions 68 and 70. Some tunneling instruments can tunnel for approximately 10 cm to approximately 30 cm before resurfacing. Depending on the tunneling instrument used, incisions may be made at intervals of approximately 10 cm to approximately 30 cm to reinsert the tunneling instrument. In the illustrated embodiments, relatively small incisions are made at incision sites 94D and 94E to allow reintroduction of the tunneling instrument. Strain relief loops may optionally be formed at incision sites 94D and 94E.

Attachment elements 88A-88F are coupled to lead extensions 68 and 70 to help fix a position of lead extension 68 relative to lead extension 70, and attachment element 88G is coupled to leads 64 and 66 to help fix a relative position of lead 64 with respect to lead 66. More specifically, attachment elements 88A-88C are coupled to lead extensions 68 and 70 proximate to incision site 94A. In one embodiment, attachment elements 88D and 88E are coupled to lead extensions 68 and 70 proximate to incision sites 94D and 94E, respectively, such that attachment elements 88D and 88E may be axially displaced from each other by approximately 10 cm to approximately 30 cm. In this matter the distance D1 between attachment elements 88D and 88E may be about 10 cm to about 30 cm. Attachment element 88F is coupled to lead extensions 68 and 70 proximate to incision site 94B, and attachment element 88G is coupled to leads 64 and 66 proximate to incision site 94B.

In addition, separate leads 64 and 66 that are attached at one or more points may also support a more flexible implantation procedure. Attachment elements 88G and 88F may be coupled to leads 64 and 66 and lead extensions 68 and 70, respectively, after leads 64 and 66 are tunneled from their respective target tissue sites 84 and 86 to incision site 94B. This enables leads 64 and 66 to be implanted separately and tunneled to a target tissue site separately. If an introducer is used to introduce leads 64 and 66 into the patient, the introducer diameter (or other outer perimeter, which depends on the shape of the introducer) may be minimized as compared to introducing a lead that is pre-bifurcated because in some embodiments, the introducer may be sized to receive one lead 64 and 66 at a time.

Because leads 64 and 66 may be coupled together during implantation within patient 16, the lengths of the separated branches of leads 64 and 66 (measured from distal end 64B to attachment element 88G and from distal end 66B to attachment element 88G, respectively) may be determined upon implantation. For example, the length of the branch of lead 64 (measured from distal end 64B to attachment element 88G) may be substantially longer or shorter than the length of branch of lead 66 (measured from distal end 66B to attachment element 88G) due to differences in the size of strain relief loops 100 and 102 or the locations of target tissue sites 84 and 86. In this embodiment, the lengths of the separated branches of lead 64 and 66 are not pre-manufactured, because attachment elements 88A-88G are placed on leads 64 and 66 and lead extensions 68 and 70 after leads 64 and 66 are tunneled from their respective target tissue sites 84 and 86 to incision site 94B. This provides more flexibility than using a lead that is manufactured to have separated branches with predetermined lengths.

Attachment element 88E may be coupled to lead extensions 68 and 70 after lead extensions 68 and 70 are tunneled to incision site 94E. Similarly, attachment element 88D may be coupled to lead extensions 68 and 70 after lead extensions 68 and 70 are tunneled to incision site 94D. Furthermore, attachment elements 88A-88C may be coupled to lead extensions 68 and 70 after lead extensions 68 and 70 are tunneled to incision site 94A.

Coupling attachment elements 88A-G (collectively "attachment elements 88") to leads 64 and 66 and/or lead extensions 68 and 70 near incision sites 94A-94E may help facilitate placement of attachment elements 88 during tunneling. Leads 64 and 66 and/or lead extensions 68 and 70 may be easily accessed through incisions at each incision site 94A-94E to apply an attachment element. In one embodiment, the attachment elements may be axially attached to leads 64, 66 and/or lead extensions 68, 70, which further facilitates attachment of attachment elements at incision sites 94A-E.

In the particular configuration illustrated in FIG. 3A, attachment elements 88 are shown as sheath-like elements that are configured to engage (e.g., via friction fit) with the lead 64, 66 or lead extension 68, 70 in order to remain substantially attached to the respective leads 64, 66 or lead extensions 68, 70, and in order to help attachment elements 88 remain substantially in place. In other embodiments, attachment elements 88 may have any suitable configuration for holding a portion of a first elongated member proximate to a portion of a second elongated member, and may include other structural or adhesive elements rather than sheaths.

Attachment elements 88 help maintain portions of elongated members (e.g., leads 64 and 66 and lead extensions 68 and 70) proximate to each other near incision sites 94A-94E between neurostimulator 62 and target tissue sites 84 and 86. When interspersed along the length of the elongated members, attachment elements 88 generally help prevent cross-over between the elongated members. Even in embodiments including a fewer number of attachment elements than that shown in FIG. 3A, the attachment elements may help prevent cross-over of the elongated members. For example, an attachment element may be mechanically couple portions of leads 64, 66 or lead extensions 68, 70 that are susceptible to cross-over, such as portions of leads 64, 66 and/or lead extensions 68, 70 that traverse a region of patient 80 that undergoes a relatively large range of motion or relatively frequent motion (e.g., a back, neck, or joint of patient 80).

Both lead 64 and lead 66 include proximal portion 104A located adjacent to proximal end 64A, distal portion 104C located adjacent to distal end 64B, and middle portion 104B located between proximal portion 104A and distal portion 104C. Portions 104A-104C are approximately equal in length. Although leads 64 and 66 may have slightly different lengths in the embodiment shown in FIG. 3A, portions 104A-104C are used to approximate the locations and lengths of proximal, middle, and distal portions of both lead 64 and lead 66.

Lead extensions 68 and 70 each includes proximal portion 106A located adjacent to proximal end 68A, distal portion 106C located adjacent to distal end 68B, and middle portion 106B located between proximal portion 106A and distal portion 106C. Portions 106A-106C are approximately equal in length. Again, although lead extensions 68 and 70 may have slightly different lengths in the embodiment shown in FIG. 3A, portions 106A-106C are used to approximate the location and lengths of proximal, middle, and distal portions of both lead extension 68 and lead extension 70.

Leads 64 and 66 are coupled together by one or more attachment elements 88 along at least one of proximal portion 104A or middle portion 104B. In the embodiment shown in FIG. 4, leads 64 and 66 are coupled together by attachment element 88G on proximal portion 104A. Additionally, lead extensions 68 and 70 are coupled together by one or more attachment elements along at least one of proximal portion 106A or middle portion 106B. Lead extensions 68 and 70 are coupled together by attachment element 88F on distal portion 106C, attachment elements 88E and 88D on middle portion 106B, and attachment elements 88A-88C on proximal portion 106A.

Although one attachment element is used in the embodiment depicted in FIG. 3A to attach leads 64 and 66 together, in other embodiments, leads 64 and 66 may be attached together at any suitable number of points by any suitable number of attachment elements. The attachment elements may be positioned along at least one of proximal portions 104A or middle portions 104B of leads 64 and 66. In addition, one or more attachment elements may be located along distal portions 104C of leads 64 and 66, so long as distal ends 64B and 66B are unattached. In some embodiments, distal portions 104C of leads 64 and 66 are devoid of any attachment elements, such that the distal portions 104C define distal branches of leads 64 and 66. Although five attachment elements are shown in the embodiment of FIG. 3A to attach lead extensions 68 and 70, in other embodiments, lead extensions 68 and 70 may also be attached together at any suitable number of points by any suitable number of attachment elements, which may be located anywhere along the length of lead extensions 68 and 70 (measured from the respective proximal end 68A, 70A to the respective distal end 68B, 70B).

The length of leads 64 and 66 typically differs depending on the particular application of electrical stimulation system 61. In some embodiments, for example, leads 64 and 66 each have a length (measured from the respective proximal end 64A, 66A to the respective distal end 64B, 66B) in a range of approximately 20 cm to approximately 40 cm. Accordingly, because proximal, middle, and distal portions 104A-104C of leads 64 and 66 have approximately equal lengths, in those embodiments, each one of proximal, middle, and distal portions 104A-104C has a length in the range of approximately 7 cm to 13 cm. In this embodiment, an attachment element located on distal portion 104C of leads 64 and 66 is located within approximately 7 cm to 13 cm of distal ends 64B, 66B of leads 64 and 66, respectively, and an attachment element located on proximal portion 104A or middle portion 104B of leads 64 and 66 is located more than approximately 7 cm to 13 cm away from distal ends 64B and 66B.

In one embodiment, most distally located attachment element 88G is axially displaced from at least one of distal ends 64B or 66B of leads 64 and 66, respectively, by at least approximately 5 cm. In this manner, the length of lead 64 from distal end 64B to attachment element 88G (i.e., a first distal branch defined by lead 64) and/or the length of lead 66 from distal end 66B to attachment element 88G (i.e., a second distal branch defined by lead 66) is at least approximately 5 cm. In one embodiment, leads 64 and 66 have approximately equal lengths and the most distally located attachment element 88G is axially displaced from the distal ends 64B and 66B of both leads 64 and 66, respectively, by an equal distance (e.g., at least approximately 5 cm). In other embodiments, leads 64 and 66 may have different lengths or distal ends 64B and 66B of leads 64 and 66 may not be aligned, such as when target stimulation sites 84 and 86 may be located a different distance from the most distally located attachment element 88G. In yet another embodiment, the most distally located attachment element 88G is axially displaced from at least one of distal ends 64B or 66B of leads 64 and 66, respectively, by at least approximately 10 cm, such that the length of lead 64 from distal end 64 to attachment element 88G and/or the length of lead 66 from distal end 66B to attachment element 88G is at least approximately 10 cm.

The length of lead extensions 68 (measured from proximal end 68A to distal end 68B) may also differ depending on the particular application of electrical stimulation system 120. In some embodiments, for example, lead extension 68 has a length in a range of about 20 cm to about 100 cm. In one particular embodiment, for example, lead extension 68 has a length in a range of about 40 cm to about 50 cm. Accordingly, because proximal, middle, and distal portions 106A-106C of lead extension 68 have approximately equal lengths, in those embodiments, portions 106A-10C of lead extension 68 are each about 13 cm to about 17 cm long. Lead extension 70 may also have a length (measured from proximal end 70A to distal end 70B) in a range of about 20 cm to about 100 cm or, in one particular embodiment, in a range of about 40 cm to about 50 cm. In some embodiments, lead extensions 68 and 70 may have different lengths or may have unaligned distal ends 68B and 70B.

From another perspective, lead 64 and lead extension 68 each may effectively define a single elongated member that is used to deliver electrical stimulation therapy from neurostimulator 62 to target tissue site 84. Similarly, lead 66 and lead extension 70 each may collectively define a second elongated member that is used to deliver electrical stimulation therapy from neurostimulator 62 to target tissue site 86. FIG. 3B illustrates a schematic plan view of therapy system 61 of FIG. 3A and illustrates elongated member 108, which is defined by lead 64 and lead extension 68, and elongated member 110, which is defined by lead 66 and lead extension 70.

Elongated member 108 is divided into three approximately equal length portions: proximal portion 112A, middle portion 112B, and distal portion 112C. Proximal portion 112A is located adjacent to neurostimulator 62. Distal portion 112C is located adjacent to target tissue site 84, and middle portion 112B is located between proximal portion 112A and distal portion 112C. Elongated member 110 is divided into three approximately equal portions: proximal portion 114A, middle portion 114B, and distal portion 114C. Proximal portion 114A is located adjacent to neurostimulator 62. Distal portion 114C is located adjacent to target tissue site 86, and middle portion 114B is located between proximal portion 114A and distal portion 114C. While portions 112A-112C and 114A-114C are not drawn to scale in FIG. 3B, portions 112A-112C and 114A-114C may appear to have different sizes due to the length required to make strain relief loops 96, 100 and 102 and the length looped around neurostimulator 62.

Attachment elements 88A-C attach proximal portion 112A of elongated member 108 to proximal portion 114A of elongated member 110. Attachment elements 88D-88E attach middle portions 112B and 114B, and attachment elements 88F and 88G attach distal portions 112C and 114C.

FIG. 4 is a schematic plan view of therapy system 120, which includes neurostimulator 122 coupled to neurostimulation lead 124, which extends from proximal end 124A to distal end 124B, and neurostimulation lead 126, which extends from proximal end 126A to distal end 126B. In the illustrated embodiment, leads 124 and 126 are implanted in the neck of patient 128. Proximal end 124A of lead 124 is coupled to neurostimulator 122 which is implanted in the head of patient 128, and distal end 124B is implanted proximate to target tissue site 130 in the neck or the head of patient 128. In the illustrated embodiment, proximal end 124A of lead 124 is directly coupled to neurostimulator 122. However, in other embodiments, lead 124 may be coupled indirectly to neurostimulator 122 via a lead extension that is coupled to neurostimulator 122. Proximal end 126A of lead 126 is coupled to neurostimulator 122 (or a lead extension that is coupled to neurostimulator 122), which is implanted in the back of patient 128, and distal end 126B is implanted proximate to target tissue site 132 in the neck or head of patient 128. In the illustrated embodiment, proximal end 126A of lead 126 is directly connected to neurostimulator 122. As with lead 124, in other embodiments, lead 126 may be indirectly connected to neurostimulator 122 via a lead extension.

Target tissue sites 130 and 132 may be, for example, in occipital region 29 (FIG. 1B) near an occipital nerve or a trigeminal nerve of patient 128. Additionally, target tissue sites 130 and 132 may be located on opposite sides of the patient's midline 134. Midline 134 is a schematic representation of the line that divides patient 128 into approximately equal and symmetrical left and right halves. Delivering therapy to two target tissue sites, such as sites 130 and 132, may be used to deliver therapy to two nerve branches that branch from the same nerve. Nerves may branch into left and right branches that extend to opposite sides of midline 134, and therapy is delivered to two nerve branches on opposite sides of midline 134 (such as at target tissue sites 130 and 132). Stimulation of two nerve branches on opposite sides of midline 134 may be referred to as bilateral stimulation. Delivering therapy after nerves branch, e.g., closer to the nerve endings, may allow more targeted therapy delivery with fewer side effects. To help facilitate the delivery of therapy to two target stimulation sites 130 and 132 from leads 124 and 126, leads 124 and 126 may be attached together at one or more points via attachment elements (discussed below) to define branches 144 and 146 that enable distal ends 124B and 126B of leads 124 and 126 to be separated and unattached from each other. Because distal ends 124B and 126B of leads 124 and 126 may be implanted on opposite sides of midline 134, electrodes 134 and 136 carried by leads 124 and 126 may also be separated and unattached from each other.

Electrodes 134 carried by lead 124 are located proximate to distal end 124B of lead 124, and electrodes 136 carried by lead 126 are located proximate to distal end 126B of lead 126. Electrodes 134 and 136 permit delivery of electrical stimulation to target stimulation sites 130 and 132, respectively. Accordingly, neurostimulation lead 124 includes a first group of one or more electrical contacts to couple electrodes 134 to terminals within neurostimulator 122. Similarly, neurostimulation lead 126 includes a second group of one or more electrical contacts to couple electrodes 136 to terminals within neurostimulator 122. While four electrodes 134 are shown in the embodiment of lead 124 illustrated in FIG. 4 and four electrodes 136 are shown in the embodiment of lead 126 illustrated in FIG. 4, in other embodiments, leads 124 and 126 may include any suitable number of electrodes.

One or more incisions are made in the back of patient 128 to facilitate implantation of neurostimulator 122 and leads 124 and 126. A first incision may be made at incision site 137B. Leads 124 and 126 may be individually tunneled from incision site 137B to target tissue sites 130 and 132. From incision site 137B to incision site 137A, leads 124 and 126 may be tunneled together using a tunneling tool that creates a path large enough for both leads 124 and 126. Some tunneling instruments can tunnel for approximately 10 cm to approximately 30 cm before resurfacing. Depending on the tunneling instrument used, incisions may be made at intervals of approximately 10 cm to approximately 30 cm to reinsert the tunneling instrument. In the illustrated embodiments, the length of lead 124 between incision sites 137B and 137A is approximately 10 cm to approximately 20 cm, and the length of lead 126 between incision sites 137B and 137A is also approximately 10 cm to approximately 20 cm.

Attachment element 138 is disposed around leads 124 and 126 to fix a position of lead 124 with respect to a position of lead 126. More specifically, attachment element 138 extends from distal end 138B to proximal end 138A. Distal end 138B of attachment element 138 is coupled to leads 124 and 126 proximate to incision site 137B. Proximal end 138A of attachment element is located proximate to proximal ends 124A and 126A of leads 124 and 126, respectively. Once distal ends 124B and 126B are properly positioned at their respective target tissue sites 130 and 132, attachment element 138 may be coupled to leads 124 and 126 before leads 124 and 126 are tunneled from incision site 137B to incision site 137A. Alternatively, attachment element 138 may be disposed around leads 124 and 126 after leads are tunneled from incision site 137B to incision site 137A. For example, attachment element 138 introduced into patient 128 at incision site 137A to leads 124 and 126.

The lengths of the separated branches of leads 124 and 126 (measured from distal end 124B of lead 124 to distal end 138B of attachment element 138 and from distal end 126B of lead 126 to distal end 138B of attachment element 138, respectively) may be determined upon implantation. In this embodiment, the lengths of the separated branches of lead 124 and 126 are not pre-manufactured, because attachment element 138 is placed on leads 124 and 126 after distal ends 124B and 126B of leads 124 and 126 are properly placed at their respective target tissue sites 130 and 132. This provides more flexibility than using a lead that is manufactured to have separated branches with predetermined lengths prior to implantation.

Coupling attachment element 138 to leads 124 and 126 near incision site 137B may help facilitate placement of attachment element 138 during tunneling. Leads 124 and 126 may be easily accessed to apply attachment element 138 at this location, because an incision is made at incision site 137B to facilitate the introduction of leads 124 and 126 into patient 128. In the particular configuration illustrated in FIG. 4, attachment element 138 is shown as a sheath-like element.

In one embodiment, sheath-like attachment element 138 is rigid enough to traverse through tissue of patient 128, and may be used, for example, to define an insertion path between incision sites 137A and 137B. A needle may be used in conjunction with sheath 138 (e.g., a needle may be disposed within sheath 138) in order to provide sufficient rigidity to sheath 138 to traverse through the tissue.

Sheath-like attachment element 138 may be useful for managing leads 124 and 126. For example, leads 124 and 126 may be easily inserted and removed from sheath-like attachment element 138 with less resistance/friction as compared to inserting leads 124 and 126 directly through tissue. In particular, sheath-like attachment element 138 may define an insertion path for leads 124 and 126 through tissue of patient 16. In some embodiments, leads 124 and 126 may be removed from sheath-like attachment element 138 while leaving sheath-like attachment element 138 in place in patient 16. This may allow replacement leads to be easily inserted into attachment element 138 and may help aid in the placement of replacement leads, as necessary. Additionally, in embodiments in which leads 124 and 126 need to be removed from patient 16, it may be possible to remove leads 124 and 126 without making any incisions along the length of attachment element 138 (extending from proximal end 138A to distal end 138B) because sheath-like attachment element 138 may eliminate the need for intermediate fixation of leads 124, 126 to surrounding tissue, at least along the portions of leads 124, 126 disposed within sheath-like attachment element 138.

Sheath-like attachment element 138 may also provide the portions of leads 124 and 126 covered by sheath-like attachment element 138 with additional protection against the environment in which leads 124 and 126 are implanted. In one embodiment, the inner surface of sheath-like attachment element 138 that receives leads 124 and 126 may be slippery or may have other properties to substantially reduce friction/resistance between leads 124 and 126 and the inner surface of sheath 138 in order to help facilitate insertion of leads 124 and 126 through attachment element 138. A slippery inner surface may also aid in providing strain relief to leads 124 and 126 by allowing movement of leads 124 and 126 along the length of attachment element 138 (extending from proximal end 138A to distal end 138B) to help mitigate the stress on leads 124 and 126. Leads 124 and 126 may be subjected to stresses from many sources, such as from the biomechanics of movement of patient 16. Additionally, the outer surface of sheath-like attachment element 138 that contacts surrounding tissue within patient 16 may have surface treatments or other properties that inhibit movement within tissue and/or promote tissue ingrowth (e.g., a rough outer surface).

Sheath-like attachment element 138 may be made out of a material, such as polymer, that enables a size of attachment element 138 to be customized at the time of implant (e.g., cut to a custom length). Sheath-like attachment element 138 may include radio-opaque markers or other markers to aid in identifying and monitoring its location.

In other embodiments, attachment elements 138 may have any suitable configuration for holding a portion of a first elongated member proximate to a portion of a second elongated member, and may include other structural or adhesive elements rather than sheaths. For example, in other embodiments, attachment element 138 may be one or more clips (e.g., clips 88 of FIGS. 3A-3B) attaching leads 124 and 126 at one or more points such that leads 124 and 126 each define branches 144 and 146 that may be implanted on opposite sides of midline 134.

Attachment element 138 helps keep portions of elongated members (e.g., leads 124 and 126) proximate to each other and, in the embodiment shown in FIG. 4, attachment element 138 helps fix a relative distance between leads 124 and 126 between incision site 137B and neurostimulator 62 in order to help prevent cross-over between leads 124 and 126.

The length of leads 124 and 126 typically differs depending on the particular application of electrical stimulation system 120. In some embodiments, for example, leads 124 and 126 each have a length (measured from the respective proximal end 124A, 126A to the respective distal end 124B, 126B) in a range of approximately 20 cm to approximately 40 cm. In some embodiments in which leads 124 and 126 each have a length of about 20 cm to about 40 cm, branches 144 and 146 of leads 124 and 126, respectively, each have a length of at least 5 cm. That is, the length of lead 124 from distal end 124B to distal end 138B of attachment element 138 and/or the length of lead 126 from distal end 126B to the distal end 138B of attachment element 138 is at least approximately 5 cm. Accordingly, distal end 138B of attachment element 138 axially displaced from distal ends 124B or 126B of leads 124 and 126, respectively, by at least approximately 5 cm. As previously discussed, in some embodiments, branches 144 and 146 have different lengths.

In another embodiment, distal end 138B of attachment element 138 is axially displaced from at least one of distal ends 124B or 126B of leads 124 and 126, respectively, by at least approximately 10 cm, such that at least one branch 144 or 146 is at least approximately 10 cm.

Figure 5A:
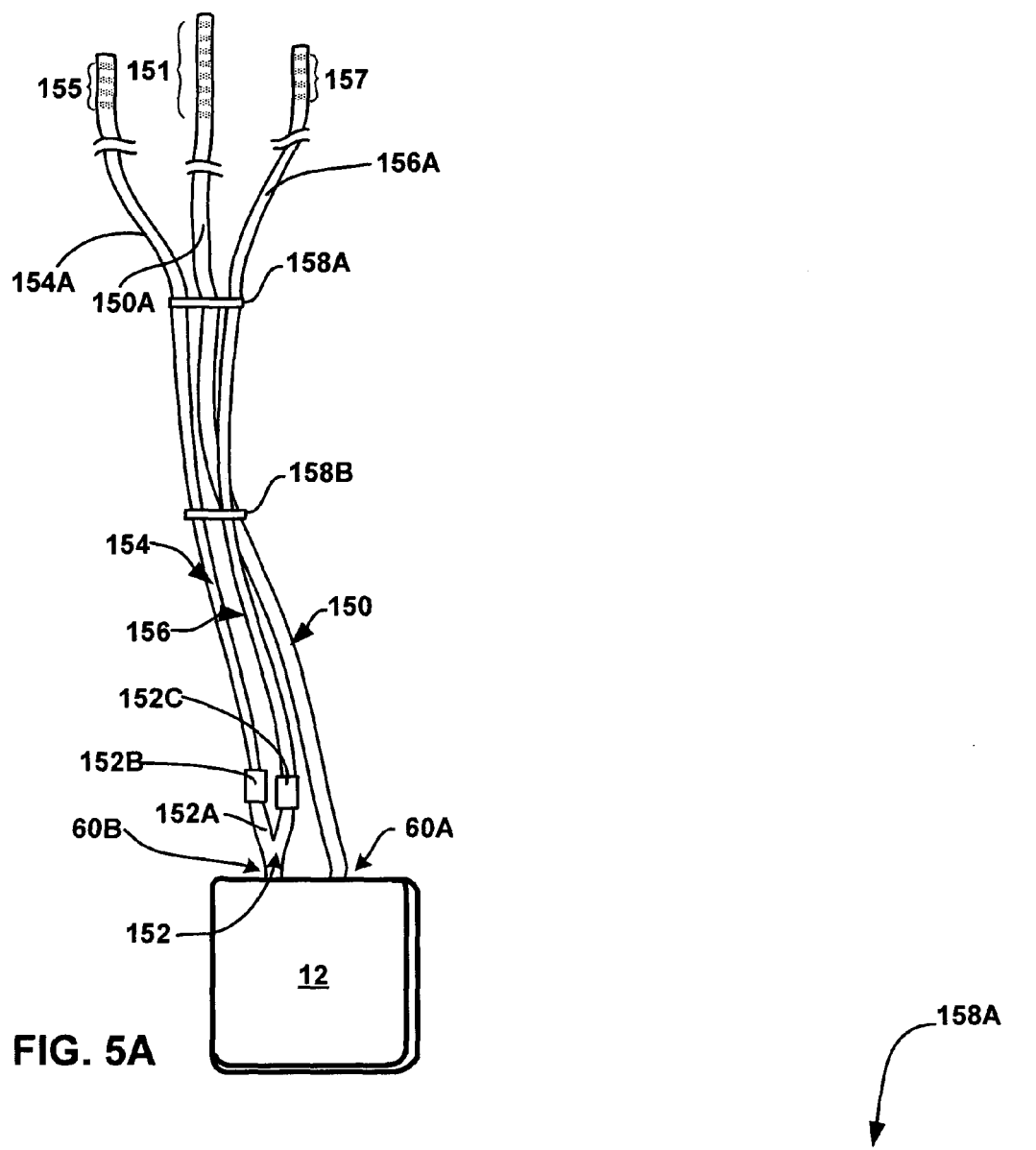
FIG. 5A is a schematic plan view of a medical device system including three leads attached together at two points.

Although FIGS. 3A-4 illustrate lead extensions that attached a single lead, in other embodiments, a bifurcated lead extension may also be attached to the electrical stimulator and coupled to one or two lead extensions or leads. FIG. 5A is a schematic view of an assembly that includes lead 150, bifurcated lead extension 152, and leads 154 and 158, which are attached to bifurcated lead extension 152. Lead 150 is coupled to connection port 60A of neurostimulator 12, while lead extension 152 is coupled to another connection port 60B. The embodiment of neurostimulator 12 shown in FIG. 5A only includes two connection ports 60A and 60B for receiving a lead or a lead extension. In order obtain an electrode configuration including three columns of electrodes, as shown in FIG. 5A, it may be useful to utilize bifurcated lead extension 152, which includes a trunk 152A that bifurcates into two arms 152B and 152C. Lead 154 is coupled to first arm 152B and lead 156 is coupled to second arm 158.

In the embodiment of neurostimulator 12 shown in FIG. 5A, first connection port 60A and second connection port 60B are each configured to receive connections to eight electrodes. Accordingly, using bifurcated lead extension 152, which connects to connection port 60B that supports eight electrodes is useful for achieving a 4-8-4 electrode configuration. In particular, lead 150 includes eight electrodes 151, lead 154 includes four electrodes 155, and lead 156 includes four electrodes 157. In alternate embodiments, medical devices including greater or fewer than two lead connection ports and/or having the ability to receive connections to greater or fewer than eight electrodes may be employed. For example, in an alternate embodiment, neurostimulator 12 may be configured to receive and support sixteen electrodes in an arrangement other than a 4-8-4 arrangement (e.g., a 5-6-5 arrangement).

Attachment elements 158A and 158B are coupled to leads 150, 154, and 156 in order to maintain the relative position between leads 150, 154, and 156. In the 4-8-4 configuration shown in FIG. 5A, cross-over between leads 150 and 156 may be desirable. Attachment element 158B may be useful for maintaining the cross-over between leads 150 and 156 without resulting in excessive rubbing between leads 150 and 156.

Attachment element 158A may be useful for attaching leads 150, 154, and 156 together and for defining branches 150A, 154A, and 156A of leads 150, 154, and 156, respectively, which are configured to extend to different therapy deliver sites within a patient. However, in some therapy programs, two or more of branches 150A, 154A, and 156A may be implanted proximate to the same target tissue site.

Figure 5B:
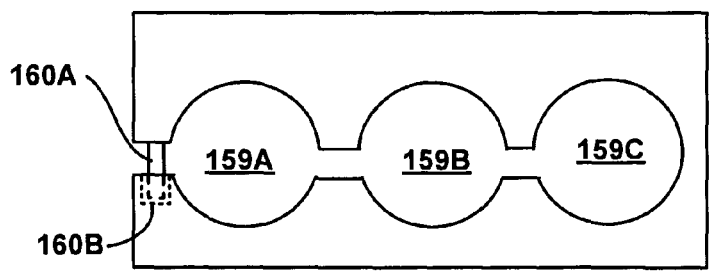
FIG. 5B is a plan view of an attachment element shown in FIG. 5A, which is an embodiment of a clip-like attachment element that may be used to attach elongated members together.

FIG. 5B is a plan view of attachment element 158A, which is an embodiment of a clip-like attachment element that may be used to attach elongated members (e.g., leads 150, 154, and 156). Attachment element 158B is similar in structure to attachment element 158B. In the closed position, as shown in FIG. 5B, attachment element 158A defines three openings 159A-C that are each configured to receive one of leads 150, 154, and 156. In other embodiments, attachment element 158A may include any suitable number of openings 159A-C, which may depend, for example, on the number of leads or other elongated members that are to be attached by attachment element 158A. Attachment element 158A may be formed of a flexible biocompatible material, such as a biocompatible polymer, which may allow for some relative movement between leads 150, 154, and 156 that are disposed in openings 159A-C. However, openings 159A-C still maintain leads 150, 154, and 156 in a substantially fixed relationship with respect to each other because attachment element 158A still prevents leads 150, 154, and 156 from unintentionally crossing over each other.

Attachment element 158A may be secured in the closed position via any suitable method. In the embodiment shown in FIG. 5B, attachment clip 158A includes a fixation pin 160A that is configured to be received in opening 160B, which engages with pin 160A to secure attachment clip 158A in a closed position.

Figure 6:
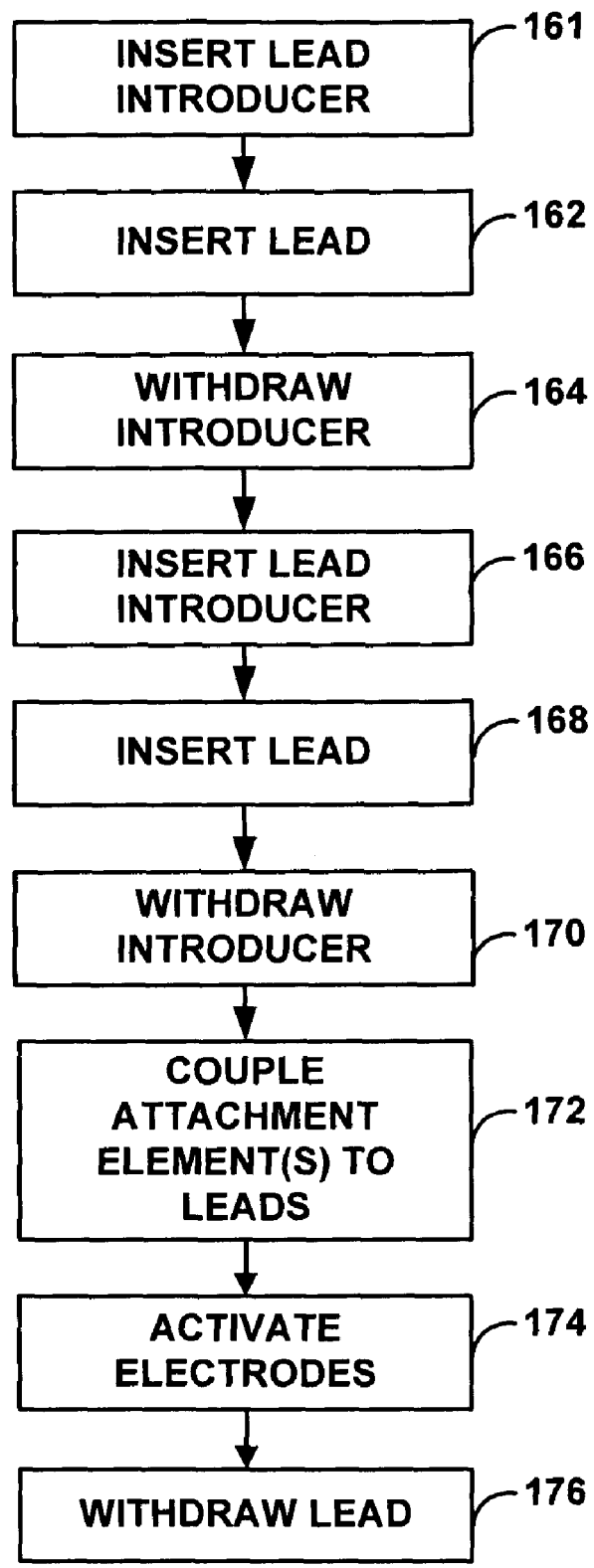
FIG. 6 is a flow diagram illustrating a process for percutaneously implanting two leads including an attachment element in accordance with one embodiment of the invention.

FIG. 6 is a flow diagram illustrating a process for percutaneously implanting two leads including one or more attachment elements to hold one or more portion of a first lead proximate to one or more portion of a second lead. While the process shown in FIG. 6 is described with respect to leads 124 and 126 of FIG. 4, in other embodiments, the elongated member may be, for example, leads 14 and 15 of FIGS. 1A, 1B, and 2, leads 64 and 66 of FIG. 3A, lead extensions 68 and 70 of FIG. 3A, or elongated members 108 and 110 of FIG. 3B. In addition, the process shown in FIG. 6 may be used to implant any suitable assembly including two or more leads and an attachment element. Furthermore, while the process is described with reference to implanting leads 124 and 126 proximate to target stimulation site 130 and 132 of FIG. 4, in other embodiments, leads 124 and 126 may be implanted proximate to any suitable target stimulation sites or target tissue sites.

Initially, an introducer needle assembly is inserted into patient 128 (161) via incision site 137B and guided to target neurostimulation site 130. The needle assembly may include a needle and an introducer stylet fitted into a lumen defined by the needle. In one embodiment, the lumen has a diameter between 14 and 20 gauge to allow the needle to receive the introducer stylet. The introducer stylet may fill the lumen of the needle, preventing tissue coring. In some instances, the needle may include a straight needle for sacral implantation or a modified Tuohy needle for epidural applications, which has an opening that is angled approximately 45 degrees so that an instrument passing through the needle exits at an angle.

The lead introducer may be inserted (161) by a variety of techniques not limited to the technique described above. For example, in some embodiments, the lead introducer may be inserted percutaneously, rather than through incision site 137B. Lead 124 is inserted (162) into a lumen of the introducer and advanced through the introducer. Lead 124 is typically advanced through the introducer until electrodes 134 reach tissue proximate to target stimulation site 130. Once neurostimulation lead 124 reaches target stimulation site 130, the lead introducer (or sheath, if a sheath is used) is withdrawn (164).

A lead introducer is inserted at incision site 137B to facilitate the introduction of lead 126 using the same (or a similar) technique described with respect in the introduction of lead 124 (166). The same or similar needle introducer may be sued to facilitate the introduction of lead 126. However, the introducer needle may need to be repositioned to implant lead 126 proximate to a different target tissue site 132. Lead 126 is inserted (168) into a lumen of the introducer and advanced through the introducer. Lead 126 is typically advanced through the introducer until electrodes 136 reach tissue proximate to target stimulation site 132. Once neurostimulation lead 126 reaches target stimulation site 132 the lead introducer (or sheath, if a sheath is used) is withdrawn (170).

After electrodes 134 of neurostimulation lead 124 have been properly placed proximate to target tissue site 130 and electrodes 136 of neurostimulation lead 126 have been properly placed proximate to target tissue site 132, proximal ends 124A and 126A of lead 124 and 126, respectively, are coupled to a neurostimulator 122. In one embodiment, lead extensions may be provided to couple leads 124 and 126 to neurostimulator 122.

In the embodiment of therapy system 120 shown in FIG. 4, neurostimulator 122 is implanted in the back of patient 128. In order to couple leads 124 and 126 to neurostimulator 122, proximal end 124A of lead 124 and proximal end 126 of lead 126 are tunneled from incision site 137B to incision site 137A proximate to neurostimulator 122. Prior to tunneling, attachment element 138 is coupled to lead 124 and 126 proximate to incision site 137B (172). Incision site 137B allows easy access to lead 124 and 126, which aids in coupling attachment element 138 to leads 124 and 126.

After attachment element 138 has been coupled to leads 124 and 126, leads 124 and 126 may be tunneled together from incision site 137B to incision site 137A proximate to neurostimulator 122. Leads 124 and 126 may be tunneled together using a tunnel tool that creates a path large enough for both leads 124 and 126. Alternatively, leads 124 and 126 may be tunneled individually from incision site 137B to incision site 137A, and attachment element 138 may be coupled to leads 124 and 126 after the tunneling to incision site 137A. For example, attachment element 138 may be tunneled around leads 124 and 126 or, if attachment element 138 is a relatively small clip (rather than a long sheath as shown in FIG. 4), attachment element 138 may be disposed around leads 124 and 126 at incision site 137B. At incision site 137A proximate to neurostimulator 122, electrodes 134 on lead 124 and electrodes 136 on lead 126 may be activated (174) to provide therapy to patient 128 by mechanically and electrically coupling proximal ends 124A and 126A of leads 124 and 126, respectively, to neurostimulator 122.

Some therapy applications may require that electrodes 134 of neurostimulation lead 124 and electrodes 136 of neurostimulation lead 126 be activated for only a short period of time, e.g., for trial stimulation, sometimes referred to as screening. On the other hand, the selected therapy application may require that leads 124 and 126 be implanted chronically for a number of years. In either case, it may become necessary to remove neurostimulation leads 124 and 126 from patient 68.

Neurostimulation leads 124 and 126 may be withdrawn from patient 128 (176). In one embodiment, leads 124 and 126 may be removed via incision site 137B. Proximal ends 124A and 126A may be detached from neurostimulator 122 and leads 124 and 126 coupled by attachment element 138 may be removed together via incision site 137B. In another embodiment, the extraction force may separate leads 124 and 126, allowing leads 124 and 126 to be explanted separately. In yet another embodiment, attachment element 138 may be detached from leads 124 and 126 prior to explantation.

A set of leads including one or more attachment element in accordance with the invention may be useful for various electrical stimulation systems, including systems for achieving bilateral stimulation. For example, the lead may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. In addition, the fixation element arrangement described herein may also be useful for fixing a catheter, such as a drug deliver catheter which delivers therapy to a target drug delivery site.

In some embodiments, implantable medical elongated members that are attached at one or more points may be coupled to different medical devices. For example, a first lead may be coupled to a sensing device while a second lead that is attached to the first lead may be coupled to an electrical stimulator. As another example, a lead may be coupled to a sensing device and a catheter that is attached to the lead may be coupled to a fluid delivery device.

Many embodiments of the invention have been described. As previously mentioned, the distances between attachment elements as well as the lengths of the branches defined between a distal end of each lead and a most distal attachment element for each of the embodiments are provided as embodiments of an arrangement between attachment elements of an elongated member, and are not intended to limit the scope of the present invention.

Various modifications may be made without departing from the scope of the claims. For example, the present invention further includes within its scope methods of making and using systems and leads for neurostimulation, as described herein, as well as methods of making and using elongated members for therapy systems. Also, the elongated members described herein may have a variety of therapy applications, such as fluid delivery to a target tissue site or other electrical stimulation applications (e.g., sensing or delivery of cardiac electrical stimulation, including paces, pulses, and shocks). These and other embodiments are within the scope of the following claims.

The invention claimed is:

1. A medical device system comprising:
    a first implantable medical elongated member configured to couple to a medical device and deliver a therapy from the medical device to a first target tissue site in a patient, the first elongated member comprising a first distal end, a first proximal section adjacent to a first proximal end, a first distal section adjacent to the first distal end, and a first middle section located between the first proximal section and the first distal section;
    a second implantable medical elongated member configured to couple to the medical device and deliver the therapy from the medical device to a second target tissue site in the patient, the second elongated member comprising a second distal end, a second proximal section adjacent to a second proximal end, a second distal section adjacent to the second distal end, and a second middle section located between the second proximal section and the second distal section, wherein the first and second implantable medical elongated members are configured to be separately implanted within the patient;
    an introducer configured to receive at least one of the first implantable medical elongated member or the second implantable medical elongated member; and
    an attachment element coupled to the first proximal section and the first middle section of the first elongated member and the second proximal section and the second middle section of the second elongated member to attach the first elongated member and the second elongated member at an attachment point, the first elongated member defining a first branch extending between the attachment element and the first distal end, and the second elongated member defining a second branch extending between the attachment element and the second distal end, wherein the first branch and the second branch are unattached, and the attachment element is separate from the introducer, and
    wherein the attachment element is configured to permit movement of the first and second implantable medical elongated members relative to the attachment element.

2. The medical device system of claim 1, wherein the first target tissue site is different than the second target tissue site.

3. The medical device system of claim 1, wherein the first proximal section, the first distal section, and the first middle section have approximately equal lengths, and wherein the second proximal section, the second distal section, and the second middle section have approximately equal lengths.

4. The medical device system of claim 1, wherein the attachment element includes a sutureless attachment element.

5. The medical device system of claim 4, wherein the sutureless attachment element includes at least one of an adhesive element, a clip or a sheath.

6. The medical device system of claim 1, wherein the first elongated member comprises a first lead comprising a first electrode proximate to the first distal end, and wherein the second elongated member comprises a second lead comprising a second electrode proximate to the second distal end, the attachment point being proximal to the first and second electrodes.

7. The medical device system of claim 6, wherein a first position of the first electrode is unfixed with respect to a second position of the second electrode.

8. The medical device system of claim 1, wherein the attachment element comprises a first attachment element, and the assembly further comprises a second attachment element axially displaced from the first attachment element.

9. The medical device system of claim 1, wherein the first elongated member comprises a first fluid delivery conduit and the second elongated member comprises a second fluid delivery conduit.

10. The medical device system of claim 1, wherein the attachment element is located at least approximately five centimeters from at least one of the first distal end of the first elongated member or the second distal end of the second elongated member, 11. The medical device system of claim 10, wherein the attachment element is located at least approximately ten centimeters from at least one of the first distal end of the first elongated member or the second distal end of the second elongated member.

12. The medical device system of claim 1, wherein the first elongated member comprises a first lead extension comprising the first distal end, the first distal end being configured to couple to at least a first lead comprising a first set of one or more electrodes to electrically connect the first set of one or more electrodes to the medical device.

13. The medical device system of claim 12, wherein the first lead extension has a length of about twenty centimeters to about one hundred centimeters.

14. The medical device system of claim 12, wherein the second elongated member comprises a second lead extension comprising the second distal end, the second distal end being configured to couple to at least a second lead comprising a second set of one or more electrodes to electrically connect the second set of one or more electrodes to the medical device.

15. The medical device system or claim 1, wherein the first elongated member comprises a first lead coupled to a first lead extension, the first distal end of the first elongated member being located on the first lead, and the second elongated member comprises a second lead coupled to a second lead extension, the second distal end of the second elongated member being located on the second lead.

16. The medical device system of claim 1, wherein the first and second branches have substantially equal lengths.

17. The medical device system of claim 1, wherein the first and second branches have different lengths.

18. A medical device system comprising:
a first implantable medical elongated member configured to couple to a first medical device and comprising a first distal end, a first proximal section adjacent to a first proximal end, a first distal section adjacent to the first distal end, and a first middle section located between the first proximal section and the first distal section;
a second implantable medical elongated member configured to couple to a second medical device and comprising a second distal end, a second proximal section adjacent to a second proximal end, a second distal section adjacent to the second distal end, and a second middle section located between the second proximal section and the second distal section, wherein the first and second implantable medical elongated members are configured to be separately implanted within the patient;
an introducer configured to receive at least one of the first implantable medical elongated member or the second implantable medical elongated member; and
an attachment element coupled to attach the first proximal section and the first middle section of the first elongated member and the second proximal section and the second middle section of the second elongated member at an attachment point, the first elongated member defining a first branch extending between the attachment element and the first distal end, and the second elongated member defining a second branch extending between the attachment element and the second distal end, wherein the first branch and the second branch are unattached, and the attachment element is separate from the introducer, and
wherein the attachment element is configured to permit movement of the first and second implantable medical elongated members relative to the attachment element.

19. The medical device system of claim 18, wherein the first medical device and the second medical device each comprise at least one of an electrical stimulator, a fluid delivery device or a sensing device.

20. A method comprising:
inserting a first implantable medical elongated member within a patient such that a first distal end of the first elongated member resides at a first target tissue site within the patient, wherein the first elongated member comprises a first proximal section adjacent to a first proximal end, a first distal section adjacent to the first distal end, and a first middle section located between the first proximal section and the first distal section;
inserting a second implantable medical elongated member within a patient such that a second distal end of second elongated member resides at a second target tissue site within the patient, wherein the second elongated member comprises a second proximal section adjacent to a second proximal end, a second distal section adjacent to the second distal end, and a second middle section located between the second proximal section and the second distal section, wherein the first and second elongated members are separately inserted within the patient; and
after inserting the first and second implantable medical elongated members, coupling an attachment element to the first proximal section and the first middle section of the first elongated member and the second proximal section and the second middle section of the second elongated member to attach the first and second elongated members at an attachment point displaced from the first distal end of the first elongated member and the second distal end of the second elongated member such that the first and second elongated members define respective branches extending between the attachment point and the first and second target tissue sites.

21. The method of claim 20, wherein the attachment element is configured to permit movement of the first and second implantable medical elongated members relative to the attachment element.

22. The method of claim 20, wherein inserting the first elongated member into the patient comprises introducing an introducer into the patient and inserting the first elongated member into a lumen of the introducer, and wherein inserting the second elongated member comprises, after inserting the first elongated member, inserting the second elongated member into the lumen of the introducer.

23. The method of claim 20, wherein each of the first elongated member and the second elongated member comprises at least one of a lead comprising an electrode or a fluid delivery conduit.

24. The method of claim 20, further comprising coupling the first elongated member and the second elongated member to a medical device.

25. The method of claim 24, wherein the medical device is at least one of an electrical stimulator, a sensor, or a fluid delivery device.

26. The method of claim 24, wherein coupling the first elongated member and the second elongated member to a medical device comprises coupling the first elongated member to a first medical device and coupling the second elongated member to a second medical device.

27. The method of claim 20, further comprising coupling a first extension to a first proximal end of the first elongated member.

28. The method of claim 20, further comprising advancing a first proximal end of the first elongated member to a medical device implant site and advancing a second proximal end of the second elongated member to the medical device implant site.

29. The method of claim 20, wherein the attachment element is a first attachment element and the method further comprises coupling a second attachment element to the first elongated member and the second elongated member at a second attachment point.

30. The method of claim 20, further comprising positioning the first and second elongated members to achieve bilateral stimulation of a nerve of the patient.

31. The method of claim 20, wherein the first and second target tissue sites are on opposite sides of a midline of the patient.

32. A. method comprising:
inserting a first lead configured to deliver electrical stimulation from an electrical stimulator to a first target tissue site in an occipital region of a patient into a body of the patient, wherein the first lead comprises:
a first lead body extending between a first proximal end configured to couple to the electrical stimulator and a first distal end; and
a first electrode proximate to the first distal end;
inserting a second lead configured to deliver electrical stimulation from the electrical stimulator to a second target tissue site in the occipital region of the patient into the body of the patient, wherein the first and second leads are separately inserted within the patient and wherein the second lead comprises:
a second lead body extending between a second proximal end configured to couple to the electrical stimulator and a second distal end; and
a second electrode proximate to the second distal end; and
after inserting the first and second leads into the body of the patient, coupling an attachment element to the first and second lead bodies at an attachment point displaced from the first distal end of the first lead body and the second distal end of the second lead body such that the first and second lead bodies define respective branches extending between the attachment point and the first and second target tissue sites.

33. The method of claim 32, wherein the attachment element is configured to permit movement of the first and second leads relative to the attachment element.

34. The method of claim 32, further comprising coupling a first lead extension to the first proximal end of the first lead body.

35. The method of claim 32, wherein the attachment element is located at least approximately five centimeters from at least one of the first distal end of the first lead body or the second distal end of the second lead body.

36. The method of claim 32, wherein the first and second target tissue sites are proximate to an occipital or a trigeminal nerve on opposite sides of a midline of the patient.

* * * * *